(12) United States Patent
Gould

(10) Patent No.: US 8,778,931 B2
(45) Date of Patent: Jul. 15, 2014

(54) SUBSTITUTED HYDROXAMIC ACIDS AND USES THEREOF

(75) Inventor: Alexandra E. Gould, Cambridge, MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 13/330,774

(22) Filed: Dec. 20, 2011

(65) Prior Publication Data

US 2012/0165316 A1 Jun. 28, 2012

Related U.S. Application Data

(60) Provisional application No. 61/426,330, filed on Dec. 22, 2010.

(51) Int. Cl.
C07D 401/06 (2006.01)
A61K 31/55 (2006.01)

(52) U.S. Cl.
USPC ...... 514/213.01; 514/307; 514/323; 540/593; 546/146; 546/201

(58) Field of Classification Search
None
See application file for complete search history.

(56) References Cited

U.S. PATENT DOCUMENTS

| | | | |
|---|---|---|---|
| 6,232,320 | B1 | 5/2001 | Stewart et al. |
| 6,541,661 | B1 | 4/2003 | Delorme et al. |
| 6,784,187 | B2 | 8/2004 | Wentland |
| 7,250,514 | B1 | 7/2007 | Xiao |
| RE39,850 | E | 9/2007 | Delorme et al. |
| 2003/0187009 | A1 | 10/2003 | Wentland |
| 2005/0148613 | A1 | 7/2005 | Van Emelen et al. |
| 2006/0004041 | A1 | 1/2006 | Cummings et al. |
| 2006/0058553 | A1 | 3/2006 | Leahy et al. |
| 2007/0213392 | A1 | 9/2007 | Miller et al. |
| 2011/0039827 | A1 | 2/2011 | Blackburn et al. |
| 2011/0046157 | A1 | 2/2011 | Blackburn et al. |
| 2012/0053201 | A1 | 3/2012 | Blackburn et al. |
| 2012/0165316 | A1 | 6/2012 | Gould |

FOREIGN PATENT DOCUMENTS

| | | | |
|---|---|---|---|
| EP | 2100879 A1 * | 9/2009 | |
| WO | WO 99/62908 A2 | 12/1999 | |
| WO | WO 00/75145 A1 | 12/2000 | |
| WO | WO 02/36573 A2 | 5/2002 | |
| WO | WO 2004/082638 A2 | 9/2004 | |
| WO | WO 2005/108367 A1 * | 11/2005 | |
| WO | WO 2007/115408 A1 | 10/2007 | |
| WO | WO 2007/115410 A1 | 10/2007 | |
| WO | WO 2009/037001 A4 | 3/2009 | |
| WO | WO 2009/112550 A1 | 9/2009 | |
| WO | WO 2009/129335 A2 | 10/2009 | |
| WO | WO 2010/151317 A1 | 12/2010 | |
| WO | WO 2010/151318 A1 | 12/2010 | |
| WO | WO 2012/027564 A1 | 3/2012 | |
| WO | WO 2012/088015 A2 | 6/2012 | |

OTHER PUBLICATIONS

International Search Report and Written Opinion of the International Searching Authority dated Jan. 20, 2012 issued in International Application No. PCT/US2011/49136, which corresponds to U.S. Appl. No. 13/217,401.
International Search Report and Written Opinion of the International Searching Authority dated Aug. 23, 2010 issued in International Application No. PCT/US2010/01801, which corresponds to U.S. Appl. No. 12/803,169.
International Search Report and Written Opinion of the International Searching Authority dated Aug. 23, 2010 issued in International Application No. PCT/US2010/01800, which corresponds to U.S. Appl. No. 12/803,170.
International Search Report and Written Opinion of the International Searching Authority dated May 3, 2012 issued in International Application No. PCT/US2011/065985, which corresponds to U.S. Appl. No. 13/330,774.
Shinji, Chihiro, et al. "Design and synthesis of phthalimide-type histone deacetylase inhibitors," *Bioorganic &. Medicinal Chemistry Letters*, vol. 15, No. 20 (2005) pp. 4427-4431.
Yang, Xiang-Jiao, et al., "The Rpd3/Hda1 family of lysine deacetylases: from bacteria and yeast to mice and men," *Nature Reviews*, vol. 9 (Mar. 2008) pp. 206-218.
Kawaguchi, Yoshiharu, et al., "The deacetylase HDAC6 regulates aggresome formation and cell viability in response to misfolded protein stress," *Cell*, vol. 115 (Dec. 12, 2003) pp. 727-738.
Simms-Waldrip, Tiffany, et al., "The aggresome pathway as a target for therapy in hematologic malignancies," *Molecular Genetics and Metabolism*, vol. 94 (2008) pp. 283-286.

(Continued)

*Primary Examiner* — Zinna Northington Davis
(74) *Attorney, Agent, or Firm* — Millennium Pharmaceuticals, Inc.

(57) ABSTRACT

This invention provides compounds of formula (I) wherein $R^1$, $R^2$, X, p, q, m, n, and Ring C have values as described in the specification, useful as inhibitors of HDAC6. The invention also provides pharmaceutical compositions comprising the compounds of the invention and methods of using the compositions in the treatment of proliferative, inflammatory, infectious, neurological or cardiovascular diseases or disorders.

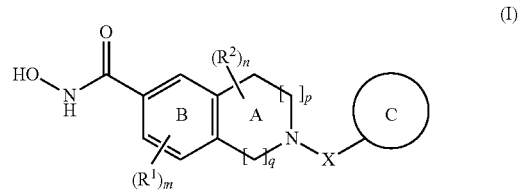

(I)

11 Claims, No Drawings

(56) References Cited

OTHER PUBLICATIONS

Kapoor, Shailendra, Letter to the Editor, "Inhibition of HDAC6-dependent carcinogenesis: emerging, new therapeutic options besides belinostat," *International Journal of Cancer*, vol. 124 (2009) p. 509.

Iwata, Atsushi, et al., "HDAC6 and microtubules are required for autophagic degradation of aggregated huntingtin," *The Journal of Biological Chemistry*, vol. 280, No. 48 (Dec. 2, 2005) pp. 40282-40292.

Ding, Wen-Xing, et al., "Linking of autophagy to ubiquitin-proteasome system is important for the regulation of endoplasmic reticulum stress and cell viability," *The American Journal of Pathology*, vol. 171, No. 2 (Aug. 2007) pp. 513-524.

Park, Jung-Hyun, et al. "Class II histone deacetylases play pivotal roles in heat shock protein 90-mediated proteasomal degradation of vascular endothelial growth factor receptors," *Biochemical and Biophysical Research Communications*, vol. 368 (2008) pp. 318-322.

Carta, Sonia, et al., "Histone deacetylase inhibitors prevent exocytosis of interleukin-1β-containing secretory lysosomes: role of microtubules," *Blood*, vol. 108, No. 5 (Sep. 1, 2006) pp. 1618-1626.

Mendrysa, Susan M., et al., "An integrated genetic-genomic approach for the identification of novel cancer loci in mice sensitized to c-Myc-induced apoptosis," *Genes & Cancer*, vol. 1, No. 5 (2010) pp. 465-479.

Namdar, Mandana, et al., "Selective inhibition of histone deacetylase 6 (HDAC6) induces DNA damage and sensitizes transformed cells to anticancer agents," *Proceedings of the National Academy of Sciences*, vol. 107, No. 46 (Nov. 16, 2010) (published on-line before print on Oct. 29, 2010 at: http://www.pnas.org/cgi/doi/10.1073/pnas.1013754107).

Tran, Andy Dong-Anh, et al., "HDAC6 deacetylation of tubulin modulates dynamics of cellular adhesions," *Journal of Cell Science*, vol. 120, No. 8 (2007) pp. 1469-1479.

Hubbert, Charlotte, et al., "HDAC6 is a microtubule-associated deacetylase," *Nature*, vol. 417, (May 23, 2002) pp. 455-458.

Kawada, Junichi, et al., "Tubacin kills Epstein-Barr virus (EBV)-Burkitt lymphoma cells by inducing reactive oxygen species and EBV lymphoblastoid cells by inducing apoptosis," *The Journal of Biological Chemistry*, vol. 284 (Jun. 19, 2009) pp. 17102-17109 (first published online on Apr. 22, 2009 at: http://www.jbc.org/cgi/doi/10.1074/jbc.M809090200).

Kaluza, David, et al., "Class IIb HDAC6 regulates endothelial cell migration and angiogenesis by deacetylation of cortactin," *The EMBO Journal* (2011) pp. 1-15.

d'Ydewalle, Constantin, et al., "HADC6 inhibitors reverse axonal loss in a mouse model of mutant HSPB1-induced Charcot-Marie-Tooth disease," *Nature Medicine*, vol. 17, No. 8 (Aug. 2011) pp. 968-974.

Haggarty, Stephen J., et al., "Domain-selective small-molecule inhibitor of histone deacetylase 6 (HDAC6)-mediated tubulin deacetylation," *Proceedings of the National Academy of Sciences*, vol. 100, No. 8 (Apr. 15, 2003) pp. 4389-4394.

Itoh, Yukihiro, et al., "Design, synthesis, structure-selectivity relationship, and effect on human cancer cells of a novel series of histone deacetylase 6-selective inhibitors," *Journal of Medicinal Chemistry*, vol. 50 (2007) pp. 5425-5438.

Butler, Kyle V., et al., "Rational design and simple chemistry yield a superior, neuroprotective HDAC6 inhibitor, tubastatin A," *Journal of the American Chemical Society*, vol. 132 (2010) pp. 10842-10846.

Yao, Tso-Pang, "The role of ubiquitin in autophagy-dependent protein aggregate processing," *Genes & Cancer*, vol. 1, No. 7 (2010) pp. 779-786.

Li, Guoyi, et al., "HDAC6 α-tubulin deacetylase: a potential therapeutic target in neurodegenerative diseases," *Journal of the Neurological Sciences*, vol. 304 (2011) pp. 1-8.

Lee, Joo-Yong, et al., "Quality control autophagy A joint effort of ubiquitin, protein deacetylase and actin cytoskeleton," *Autophagy*, vol. 6, No. 4 (May 16, 2010) pp. 555-557.

Tapia, Monica, et al., "Impaired Function of HDAC6 slows down axonal growth and interferes with axon initial segment development," *PLoS ONE*, vol. 5, No. 9 (Sep. 2010) e12908, pp. 1-13.

Cabrero, J. Roman, et al., "Lymphocyte chemotaxis is regulated by histone deacetylase 6, independently of its deacetylase activity," *Molecular Biology of the Cell*, vol. 17 (Aug. 2006) pp. 3435-3445.

Bobrowska, Anna, et al., "Hdac6 knock-out increases tubulin acetylation but does not modify disease progression in the R6/2 mouse model of Huntington's disease," *PLoS ONE*, vol. 6, No. 6 (Jun. 2011) e20696, pp. 1-11.

Fiesel, Fabienne C., et al., "TDP-43 knockdown impairs neurite outgrowth dependent on its target histone deacetylase 6," *Molecular Neurodegeneration*, vol. 6, No. 64 (2011) pp. 1-10.

Lemon, Douglas D., et al., "Cardiac HDAC6 catalytic activity is induced in response to chronic hypertension," *Journal of Molecular and Cellular Cardiology* (2011) doi:10.1016/j.yjmcc.2011.04.005.

Olzmann, J.A., et al., "Aggresome formation and neurodegenerative diseases: therapeutic implications," *Current Medicinal Chemistry*, vol. 15 (2008) pp. 47-60.

Zhu, Jianzhong, et al., "PKC alpha regulates Sendai virus-mediated interferon induction through HDAC6 and β-catenin," *The EMBO Journal*, vol. 30 (2011) pp. 4838-4849.

Zhang, Zhenhuan, et al., "HDAC6 expression is correlated with better survival in breast cancer," *Clinical Cancer Research*, vol. 10 (Oct. 5, 2004) pp. 6962-6968.

Fiesel, Fabienne C., et al., "Knockdown of transactive response DNA-binding protein (TDP-43) downregulates histone deacetylase 6," *The EMBO Journal*, vol. 29 (2010) pp. 209-221.

Beurel, Eleonore, "HDAC6 regulates LPS-tolerance in astrocytes," *PLoS ONE*, vol. 6, No. 10 (Oct. 2011) e25804, pp. 1-8.

Mild, Yasuo, et al., "Accumulation of histone deacetylase 6, an aggresome-related protein, is specific to Lewy bodies and glial cytoplasmic inclusions," *Neuropathology*, vol. 31, No. 6 (Dec. 2011) pp. 561-568 (first published online on Feb. 1, 2011: doi:10.1111/j.1440-1789.2011.01200.x.

Kim, In Ah, et al., "Epigenetic modulation of radiation response in human cancer cells with activated EGFR or HER-2 signaling: potential role of histone deacetylase 6," *Radiotherapy and Oncology*, vol. 92 (2009) pp. 125-132.

Mellado, Begona, et al., "Molecular biology of androgen-independent prostate cancer: the role of the androgen receptor pathway," *Clinical & Transational Oncology*, vol. 11 (2009) pp. 5-10.

Bhalla, K.N., et al., "Inhibition of histone deacetylase (HDAC) 6 sensitizes human leukemia and breast cancer cells to antagonists of heat shock protein (hsp) 90 and/or bortezomib (BZ)," *Journal of Clinical Oncology*, Abstract, 2006 ASCO Annual Meeting Proceedings (Post-Meeting Edition), vol. 24, No. 18S (Jun. 20, 2006 Supplement) (2006) p. 13039.

Dompierre, Jim P., "Histone deacetylase 6 inhibition compensates for the transport deficit in Huntington's disease by increasing tubulin acetylation," *The Journal of Neuroscience*, vol. 27, No. 13 (Mar. 28, 2007) pp. 3571-3583.

Kazantsev, Aleksey G., et al., "Therapeutic application of histone deacetylase inhibitors for central nervous system disorders," *Nature Reviews*, vol. 7 (Oct. 2008) pp. 854-868.

Dhakal, Bijaya K., et al., "Uropathogenic *Escherichia coli* invades host cells via an HDAC6-modulated microtubule-dependent pathway," *Journal of Biological Chemistry*, vol. 284, No. 1 (Jan. 2, 2009) pp. 446-454.

Perez, Mar, et al., "Tau—an inhibitor of deacetylase HDAC6 function," *Journal of Neurochemistry*, vol. 109 (2009) pp. 1756-1766.

Pugacheva, Elena N., et al., "HEF1-dependent aurora A activation induces disassembly of the primary cilium," *Cell*, vol. 129 (Jun. 29, 2007) pp. 1351-1363.

Gao, Ya-sheng, et al., "The microtubule-associated histone deacetylase 6 (HDAC6) regulates epidermal growth factor receptor (EGFR) endocytic trafficking and degradation," *Journal of Biological Chemistry*, vol. 285, No. 15 (Apr. 9, 2010) pp. 11219-11226.

Tannous, Paul, et al., "Intracellular protein aggregation is a proximal trigger of cardiomyocyte autophagy," *Circulation Journal of the American Heart Association*, vol. 117 (2008) pp. 3070-3078 (published online before print Jun. 9, 2008 at: doi:10.1161/CIRCULATIONAHA.107.763870).

(56) References Cited

OTHER PUBLICATIONS

Rao, Rekha, et al., "HDAC6 inhibition enhances 17-AAG-mediated abrogation of hsp90 chaperone function in human leukemia cells," *Blood*, vol. 112, No. 5 (Sep. 1, 2008) pp. 1886-1893.

Zhou, Jun, et al., "The protein farnesyltransferase regulates HDAC6 activity in a microtubule-dependent manner," *Journal of Biological Chemistry*, vol. 284, No. 15 (Apr. 10, 2009) pp. 9648-9655.

Cha, Tai-Lung, et al., "Dual degradation of aurora A and B kinases by the histone deacetylase inhibitor LBH589 induces G2-M arrest and apoptosis of renal cancer cells," *Clinical Cancer Research*, vol. 15, No. 3 (Feb. 1, 2009) pp. 840-850.

Kozikowski, Alan P., "Functional differences in epigenetic modulators-superiority of mercaptoacetamide-based histone deacetylase inhibitors relative to hydroxamates in cortical neuron neuroprotection studies," *Journal of Medicinal Chemistry*, vol. 50 (2007) pp. 3054-3061.

Boyault, C., et al., "HDAC6, at the crossroads between cytoskeleton and cell signaling by acetylation and ubiquitination," *Oncogene*, vol. 26 (2007) pp. 5468-5476.

Saunders, L.R., et al., "Sirtuins: critical regulators at the crossroads between cancer and aging," *Oncogene*, vol. 26 (2007) pp. 5489-5504.

Li, Yu, et al., "HDAC6 is required for epidermal growth factor-induced β-catenin nuclear localization," *Journal of Biological Chemistry*, vol. 283, No. 19 (May 9, 2008) pp. 12686-12690.

Fiskus, Warren, et al., "Molecular and biologic characterization and drug sensitivity of pan-histone deacetylase inhibitor-resistant acute myeloid leukemia cells," *Blood*, vol. 112, No. 7 (Oct. 1, 2008) pp. 2896-2905.

Nawrocki, Steffan T., et al., "Aggresome disruption: a novel strategy to enhance bortezomib-induced apoptosis in pancreatic cancer cells;" *Cancer Research*, vol. 66, No. 7 (Apr. 1, 2006) pp. 3773-3781.

Boyault, Cyril, et al., "HDAC6-p97/VCP controlled polyubiquitin chain turnover," *The EMBO Journal*, vol. 25 (2006) pp. 3357-3366.

Hideshima, Teru, et al., "Small-molecule inhibition of proteasome and aggresome function induces synergistic antitumor activity in multiple myeloma," *Proceedings of the National Academy of Sciences*, vol. 102, No. 24 (Jun. 14, 2005) pp. 8567-8572.

Rivieccio, Mark A., et al., "HDAC6 is a target for protection and regeneration following injury in the nervous system," *Proceedings of the National Academy of Sciences*, vol. 106, No. 46 (Nov. 17, 2009) pp. 19599-19604.

Parmigiani, R.B., et al., "HDAC6 is a specific deacetylase of peroxiredoxins and is involved in redox regulation," *Proceedings of the National Academy of Sciences*, vol. 105, No. 28 (Jul. 15, 2008) pp. 9633-9638.

Matthias, Patrick, et al., "HDAC6 a new cellular stress surveillance factor," *Cell Cycle*, vol. 7, No. 1 (Jan. 1, 2008) pp. 7-10.

Rodriguez-Gonzalez, Agustin, et al., "Role of the aggresome pathway in cancer: targeting histone deacetylase 6-dependent protein degradation," *Cancer Research*, vol. 68, No. 8 (Apr. 15, 2008) pp. 2557-2559.

Lee, Yi-Shan, et al., "The cytoplasmic deacetylase HDAC6 is required for efficient oncogenic tumorigenesis," *Cancer Research*, vol. 68, No. 18 (Sep. 15, 2008) pp. 7561-7569.

Lee, Joo-Yong, et al., "HDAC6 controls autophagosome maturation essential for ubiquitin-selective quality-control autophagy," *The EMBO Journal*, vol. 29 (2010) pp. 969-980.

Kamemura, Kazuo, et al., "Effects of downregulated HDAC6 expression on the proliferation of lung cancer cells," *Biochemical and Biophysical Research Communications*, vol. 374 (2008) pp. 84-89.

Crabbe, Tom, et al., "The P13K inhibitor arsenal: choose your weapon!" *TRENDS in Biochemical Sciences*, vol. 32, No. 10 (2007) pp. 45-456.

Pandey, Udai Bhan, et al., "HDAC6 rescues neurodegeneration and provides an essential link between autophagy and the UPS," *Nature*, vol. 447 (Jun. 14, 2007) pp. 859-863.

Zhang, Xiaochong, et al., "HDAC6 modulates cell motility by altering the acetylation level of cortactin," *Molecular Cell*, vol. 27 (Jul. 20, 2007) pp. 197-213.

Deribe, Yonathan Lissanu, et al., "Regulation of epidermal growth factor receptor trafficking by lysine deacetylase HDAC6," *Science Signaling*, vol. 2, No. 102 (Dec. 22, 2009) ra84 pp. 1-12 (published online at: DOI: 10.1126/scisignal.2000576).

Park, Jung-Hyun, et al., "Inhibitors of histone deacetylases induce tumor-selective cytotoxicity through modulating Aurora-A kinase," *Journal of Molecular Medicine*, vol. 86 (2008) pp. 117-128.

Bazzaro, Martina, et al., "Ubiquitin proteasome system stress underlies synergistic killing of ovarian cancer cells by bortezomib and novel HDAC6 inhibitor," *Clinical Cancer Research*, vol. 14, No. 22 (Nov. 15, 2008) pp. 7340-7347.

Shan, Bin, et al., "Requirement of HDAC6 for transforming growth factor-β1-induced epithelial-mesenchymal transition," *Journal of Biological Chemistry*, vol. 283, No. 30 (Jul. 25, 2008) pp. 21065-21073.

Kalveram, Birte, et al., "The ubiquitin-like modifier FAT10 interacts with HDAC6 and localizes to aggresomes under proteasome inhibition," *Journal of Cell Science*, vol. 121, No. 24 (2008) pp. 4079-4088.

Valenzuela-Fernandez, Agustin, et al., "HDAC6: a key regulator of cytoskeleton, cell migration and cell-cell interactions," *Trends in Cell Biology*, vol. 18, No. 6 (2008) pp. 291-297.

Du, Gulping, et al., "To prevent neurodegeneration HDAC6 uses different strategies for different challenges," *Communicative & Integrative Biology*, vol. 4, No. 2 (Mar./Apr. 2011) pp. 139-142.

Paris, Marielle, et al., "Histone deacetylase inhibitors: from bench to clinic," *Journal of Medicinal Chemistry*, vol. 51, No. 6 (Mar. 27, 2008) pp. 1505-1529.

Santo L. et al., "Selective Inhibition of HDAC6 with a New Prototype Inhibitor (ACY-1215) Overcomes Bortezomib Resistance In Multiple Myeloma (MM)," *Blood*, (ASH Annual Meeting Abstracts) (2010) 116: Abstract 2997.

Office Action dated Jul. 9, 2012 in pending U.S. Appl. No. 13/217,401.

Office Action dated Feb. 21, 2013 in pending U.S. Appl. No. 12/803,169.

Hubbs, Jed L. et al., "Amino Acid Derivatives as Histone Deacetylase Inhibitors," *Bioorganic & Medicinal Chemistry Letters*, vol. 18 (2008), pp. 34-38.

George, Dawn et al., "Discovery of Thieno[2,3-c]pyridines as Potent COT Inhibitors," *Bioorganic & Medicinal Chemistry Letters*, vol. 18 (2008), pp. 4952-4955.

Office Action dated Jan. 14, 2013 in pending U.S. Appl. No. 12/803,170.

Weinmann, Hilmar et al., "Histone Deacetylase Inhibitors: A Survey of Recent Patents," *Expert Opinion*, vol. 15, No. 12 (2005), pp. 1677-1690.

Office Action dated Oct. 10, 2013 in pending U.S. Appl. No. 12/803,169.

Cenik, Basar et al., "Suberoylanilide Hydromamic Acid (Vorinostat) Up-Regulates Progranulin Transcription," *The Journal of Biological Chemistry*, vol. 286, No. 18 (May 6, 2011), pp. 16101-16108.

\* cited by examiner

SUBSTITUTED HYDROXAMIC ACIDS AND USES THEREOF

PRIORITY CLAIM

This application claims the benefit under 35 U.S.C. §119(e) of U.S. Provisional Patent Application Ser. No. 61/426,330, filed Dec. 22, 2010, incorporated by reference in its entirety.

FIELD OF THE INVENTION

The invention relates to compounds and methods for the selective inhibition of HDAC6. The present invention relates to compounds useful as HDAC6 inhibitors. The invention also provides pharmaceutical compositions comprising the compounds of the invention and methods of using the compositions in the treatment of various diseases.

BACKGROUND OF THE INVENTION

Histone deacetylase 6 (HDAC6) is a member of a family of amidohydrolases commonly referred as histone or lysine deacetylases (HDACs or KDACs) as they catalyze the removal of acetyl groups from the ε-amino group of lysine residues from proteins. The family includes 18 enzymes which can be divided in 3 main classes based on their sequence homology to yeast enzymes Rpd3 (Class I), Hda1 (Class II) and Sir2 (Class III). A fourth class was defined with the finding of a distinct mammalian enzyme—HDAC11 (reviewed in Yang, et al., *Nature Rev. Mol. Cell. Biol.* 2008, 9:206-218 and in Saunders and Verdin, *Oncogene* 2007, 26(37):5489-5504). Biochemically, Class I (HDAC1, 2, 3, 8) and Class II (HDAC4, 5, 6, 7, 9, 10) and Class IV (HDAC11) are $Zn^{2+}$-dependent enzymes, while Class III (SIRT1-7) are dependent on nicotinamide adenine dinucleotide ($NAD^+$) for activity. Unlike all other HDACs, HDAC6 resides primarily in the cytosol. It has 2 functional catalytic domains and a carboxy-terminal $Zn^{2+}$-finger ubiquitin binding domain that binds ubiquitinated misfolded proteins (Kawaguchi et al., *Cell* 2003, 115(6):727-738), ubiquitin (Boyaullt et al., *EMBO J.* 2006, 25(14):3357-3366), as well as ubiquitin-like FAT10 modifier (Kalveram et al., *J Cell Sci.* 2008, 121(24):4079-4088). Known substrates of HDAC6 include cytoskeletal proteins α-tubulin and cortactin; β-catenin which forms part of adherens junctions and anchors the actin cytoskeleton; the chaperone Hsp90; and the redox regulatory proteins peroxiredoxin (Prx) I and Prx II (reviewed in Boyault et al., *Oncogene* 2007, 26(37):5468-5476; Matthias et al., *Cell Cycle* 2008, 7(1):7-10; Li et al., *J Biol. Chem.* 2008, 283(19):12686-12690; Parmigiani et al., *Proc. Natl. Acad. Sci. USA* 2009, 105(28):9633-9638). Thus, HDAC6 mediates a wide range of cellular functions including microtubule-dependent trafficking and signaling, membrane remodeling and chemotactic motility, involvement in control of cellular adhesion, ubiquitin level sensing, regulation of chaperone levels and activity, and responses to oxidative stress. All of these functions may be important in tumorigenesis, tumor growth and survival as well as metastasis (Simms-Waldrip et al., *Mol. Genet. Metabolism* 2008, 94(3):283-286; Rodriguez-Gonzalez et al., *Cancer Res.* 2008, 68(8):2557-2560; Kapoor, *Int. J. Cancer* 2009, 124:509; Lee et al., *Cancer Res.* 2008, 68(18):7561-7569). Recent studies have shown HDAC6 to be important in autophagy, an alternative pathway for protein degradation that compensates for deficiencies in the activity of the ubiquitin proteasome system or expression of proteins prone to form aggregates and can be activated following treatment with a proteasome inhibitor (Kawaguchi et al., *Cell* 2003, 115(6):727-738; Iwata et al., *J. Biol. Chem.* 2005, 280(48): 40282-40292; Ding et al., *Am. J. Pathol.* 2007, 171:513-524, Pandey et al., *Nature* 2007, 447(7146):860-864). Although the molecular mechanistic details are not completely understood, HDAC6 binds ubiquitinated or ubiquitin-like conjugated misfolded proteins which would otherwise induce proteotoxic stress and then serves as an adaptor protein to traffic the ubiquitinated cargo to the microtubule organizing center using the microtubule network via its known association with dynein motor protein. The resulting perinuclear aggregates, known as aggresomes, are then degraded by fusion with lysosomes in an HDAC6- and cortactin-dependent process which induces remodeling of the actin cytoskeleton proximal to aggresomes (Lee et al., *EMBO J.* 2010, 29:969-980). In addition, HDAC6 regulates a variety of biological processes dependent on its association with the microtubular network including cellular adhesion (Tran et al., *J Cell Sci.* 2007, 120(8):1469-1479) and migration (Zhang et al., *Mol. Cell.* 2007, 27(2):197-213; reviewed in Valenzuela-Fernandez et al., *Trends Cell. Biol.* 2008, 18(6):291-297), epithelial to mesenchymal transition (Shan et al., *J. Biol. Chem.* 2008, 283 (30):21065-21073), resistance to anoikis (Lee et al., *Cancer Res.* 2008, 68(18):7561-7569), epithelial growth factor-mediated Wnt signaling via β-catenin deacetylation (Li et al., *J. Biol. Chem.* 2008, 283(19):12686-12690) and epithelial growth factor receptor stabilization by endocytic trafficking (Lissanu Deribe et al., *Sci. Signal.* 2009, 2(102): ra84; Gao et al., *J. Biol. Chem.* 2010, 285:11219-11226); all events that promote oncogenesis and metastasis (Lee et al., *Cancer Res.* 2008, 68(18):7561-7569). HDAC6 activity is known to be upregulated by Aurora A kinase in cilia formation (Pugacheva et al., *Cell* 2007, 129(7):1351-1363) and indirectly by farnesyl transferase with which HDAC6 forms a complex with microtubules (Zhou et al., *J. Biol. Chem.* 2009, 284(15): 9648-9655). Also, HDAC6 is negatively regulated by tau protein (Perez et al., *J. Neurochem.* 2009, 109(6):1756-1766).

Diseases in which selective HDAC6 inhibition could have a potential benefit include cancer (reviewed in Simms-Waldrip et al., *Mol. Genet. Metabolism* 2008, 94(3):283-286 and Rodriguez-Gonzalez et al., *Cancer Res.* 2008, 68(8):2557-2560), specifically: multiple myeloma (Hideshima et al., *Proc. Natl. Acad. Sci. USA* 2005, 102(24):8567-8572); lung cancer (Kamemura et al., *Biochem. Biophys. Res. Commun.* 2008, 374(1):84-89); ovarian cancer (Bazzaro et al., *Clin. Cancer Res.* 2008, 14(22):7340-7347); breast cancer (Lee et al., *Cancer Res.* 2008, 68(18):7561-7569); prostate cancer (Mellado et al., *Clin. Trans. Onco.* 2009, 11(1):5-10); pancreatic cancer (Nawrocki et al., *Cancer Res.* 2006, 66(7): 3773-3781); renal cancer (Cha et al., *Clin. Cancer Res.* 2009, 15(3):840-850); and leukemias such as acute myeloid leukemia (AML) (Fiskus et al., *Blood* 2008, 112(7):2896-2905) and acute lymphoblastic leukemia (ALL) (Rodriguez-Gonzalez et al., *Blood* 2008, 112(11): Abstract 1923).

Inhibition of HDAC6 may also have a role in cardiovascular disease, i.e. cardiovascular stress, including pressure overload, chronic ischemia, and infarction-reperfusion injury (Tannous et al., *Circulation* 2008, 117(24):3070-3078); bacterial infection, including those caused by uropathogenic *Escherichia coli* (Dhakal and Mulve, *J. Biol. Chem.* 2008, 284(1):446-454); neurological diseases caused by accumulation of intracellular protein aggregates such as Huntington's disease (reviewed in Kazantsev et al., *Nat. Rev. Drug Disc.* 2008, 7(10):854-868; see also Dompierre et al., *J. Neurosci.* 2007, 27(13):3571-3583; Kozikowski et al., *J. Med. Chem.* 2007, 50:3054-3061) or central nervous system trauma caused by tissue injury, oxidative-stress induced neuronal or axonal degeneration (Rivieccio et al., *Proc. Natl. Acad. Sci. USA* 2009, 106(46):19599-195604); and inflammation, including reduction of pro-inflammatory cytokine IL-1β (Carta et al., *Blood* 2006, 108(5):1618-1626), increased expression of the FOXP3 transcription factor, which induces immunosuppressive function of regulatory T-cells resulting in benefits in chronic diseases such as rheumatoid arthritis, psoriasis, multiple sclerosis, lupus and organ transplant rejection (reviewed in Wang et al., *Nat. Rev. Drug Disc.* 2009, 8(12):969-981).

Given the complex function of HDAC6, selective inhibitors could have potential utility when used alone or in combination with other chemotherapeutics such as microtubule destabilizing agents (Zhou et al., *J. Biol. Chem.* 2009, 284 (15): 9648-9655); Hsp90 inhibitors (Rao et al., *Blood* 2008, 112(5)1886-1893); inhibitors of Hsp90 client proteins, including receptor tyrosine kinases such as Her-2 or VEGFR (Bhalla et al., *J. Clin. Oncol.* 2006, 24(18S): Abstract 1923; Park et al., *Biochem. Biophys. Res. Commun.* 2008, 368(2): 318-322), and signaling kinases such as Bcr-Abl, Akt, mutant FLT-3, c-Raf, and MEK (Bhalla et al., *J. Clin. Oncol.* 2006, 24(18S): Abstract 1923; Kamemura et al., *Biochem. Biophys. Res. Commun.* 2008, 374(1):84-89); inhibitors of cell cycle kinases Aurora A and Aurora B (Pugacheva et al., *Cell* 2007, 129(7):1351-1363; Park et al., *J. Mol. Med.* 2008, 86(1): 117-128; Cha et al., *Clin. Cancer Res.* 2009, 15(3):840-850); EGFR inhibitors (Lissanu Deribe et al., *Sci. Signal.* 2009, 2(102): ra84; Gao et al., *J. Biol. Chem.* 2010, 285:11219-11226) and proteasome inhibitors (Hideshima et al., *Proc. Natl. Acad. Sci. USA* 2005, 102(24):8567-8572) or other inhibitors of the ubiquitin proteasome system such as ubiquitin and ubiqutin-like activating (E1), conjugation (E2), ligase enzymes (E3, E4) and deubiquitinase enzymes (DUBs) as well as modulators of autophagy and protein homeostasis pathways. In addition, HDAC6 inhibitors could be combined with radiation therapy (Kim et al., *Radiother. Oncol.* 2009, 92(1):125-132.

Clearly, it would be beneficial to provide novel HDAC6 inhibitors that possess good therapeutic properties, especially for the treatment of proliferative diseases or disorders.

DETAILED DESCRIPTION OF THE INVENTION

1. General Description of Compounds of the Invention

The present invention provides compounds that are effective inhibitors of HDAC6. These compounds are useful for inhibiting HDAC6 activity in vitro and in vivo, and are especially useful for the treatment of various cell proliferative diseases or disorders. The compounds of the invention are represented by formula (I):

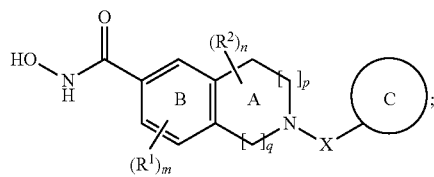

or a pharmaceutically acceptable salt thereof;
wherein:
p is 0-3 and q is 1-4, and the total of p and q is 1-4;
X is —C(O)—, —CH$_2$—, or -L$_1$-R$^3$—V$_1$—;
L$_1$ is a bond or unsubstituted or substituted C$_{1-3}$ alkylene chain;

R$^3$ is a 6-membered aromatic ring containing 0-2 nitrogen atoms which is unsubstituted or substituted with 1-2 independent occurrences of R$^4$;
each occurrence of R$^4$ is independently chloro, fluoro, cyano, hydroxy, methoxy, ethoxy, trifluoromethoxy, trifluoromethyl, methyl, or ethyl;
V$_1$ is a bond, —NH—C(O)—, —C(O)—NH—, —NH—S(O)$_2$—, or —NH—C(O)—NH—;
Ring C is a 4-7 membered heterocyclic ring containing one nitrogen atom, wherein the nitrogen atom is not the atom bound to X;
  wherein the nitrogen atom in Ring C is substituted with R$^{9b}$ and Ring C is unsubstituted or substituted by 1-4 occurrences of R$^{5b}$;
ring B is optionally further substituted with m occurrences of R$^1$;
each occurrence of R$^1$ is independently chloro, fluoro, cyano, hydroxy, methoxy, ethoxy, trifluoromethoxy, trifluoromethyl, methyl, or ethyl;
ring A is optionally further substituted with n occurrences of R$^2$;
each occurrence of R$^2$ is independently fluoro, methyl, or trifluoromethyl;
R$^{9b}$ is hydrogen, unsubstituted C(O)—O—C$_{1-6}$ aliphatic, unsubstituted C(O)—C$_{1-6}$ aliphatic, unsubstituted C(O)—C$_{3-10}$ cycloaliphatic, or unsubstituted C$_{1-6}$ aliphatic;
each occurrence of R$^{5b}$ is independently chloro, fluoro, hydroxy, methyl, ethyl, methoxy, ethoxy, trifluoromethyl, trifluoromethoxy, —C(O)NH$_2$, or —CO$_2$H;
m is 0-1; and
n is 0-2.

In another aspect, the compounds of the invention are represented by formula (I):

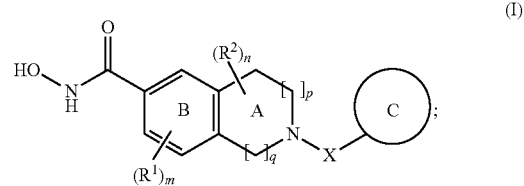

or a pharmaceutically acceptable salt thereof;
wherein:
p is 0-3 and q is 1-4, and the total of p and q is 1-4;
X is —C(O)— or -L$_1$-R$^3$—V$_1$—;
L$_1$ is a bond or unsubstituted or substituted C$_{1-3}$ alkylene chain;
R$^3$ is a 6-membered aromatic ring containing 0-2 nitrogen atoms which is unsubstituted or substituted with 1-2 independent occurrences of R$^4$;
each occurrence of R$^4$ is independently chloro, fluoro, cyano, hydroxy, methoxy, ethoxy, trifluoromethoxy, trifluoromethyl, methyl, or ethyl;
V$_1$ is a bond, —NH—C(O)—, —C(O)—NH—, —NH—S(O)$_2$—, or —NH—C(O)—NH—;
Ring C is a 4-7 membered heterocyclic ring containing one nitrogen atom, wherein the nitrogen atom is not the atom bound to X;
  wherein the nitrogen atom in Ring C is substituted with R$^{9b}$ and Ring C is unsubstituted or substituted by 1-4 occurrences of R$^{5b}$;
ring B is optionally further substituted with m occurrences of R$^1$;

each occurrence of $R^1$ is independently chloro, fluoro, cyano, hydroxy, methoxy, ethoxy, trifluoromethoxy, trifluoromethyl, methyl, or ethyl;

ring A is optionally further substituted with n occurrences of $R^2$;

each occurrence of $R^2$ is independently fluoro, methyl, or trifluoromethyl;

$R^{9b}$ is hydrogen, unsubstituted C(O)—O—$C_{1-6}$ aliphatic, unsubstituted C(O)—$C_{1-6}$ aliphatic, unsubstituted C(O)—$C_{3-10}$ cycloaliphatic, or unsubstituted $C_{1-6}$ aliphatic;

each occurrence of $R^{5b}$ is independently chloro, fluoro, hydroxy, methyl, ethyl, methoxy, ethoxy, trifluoromethyl, trifluoromethoxy, —C(O)NH$_2$, or —CO$_2$H;

m is 0-1; and n is 0-2.

2. Compounds and Definitions

Compounds of this invention include those described generally for formula (I) above, and are further illustrated by the classes, subclasses, and species disclosed herein. As used herein, the following definitions shall apply unless otherwise indicated.

As described herein, compounds of the invention may be optionally substituted with one or more substituents, such as are illustrated generally above, or as exemplified by particular classes, subclasses, and species of the invention. It will be appreciated that the phrase "optionally substituted" is used interchangeably with the phrase "substituted or unsubstituted." In general, the term "substituted", whether preceded by the term "optionally" or not, means that a hydrogen radical of the designated moiety is replaced with the radical of a specified substituent, provided that the substitution results in a stable or chemically feasible compound. The term "substitutable", when used in reference to a designated atom, means that attached to the atom is a hydrogen radical, which hydrogen atom can be replaced with the radical of a suitable substituent. Unless otherwise indicated, an "optionally substituted" group may have a substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds.

A stable compound or chemically feasible compound is one in which the chemical structure is not substantially altered when kept at a temperature from about −80° C. to about +40° C., in the absence of moisture or other chemically reactive conditions, for at least a week, or a compound which maintains its integrity long enough to be useful for therapeutic or prophylactic administration to a patient.

The phrase "one or more substituents", as used herein, refers to a number of substituents that equals from one to the maximum number of substituents possible based on the number of available bonding sites, provided that the above conditions of stability and chemical feasibility are met.

As used herein, the term "independently selected" means that the same or different values may be selected for multiple instances of a given variable in a single compound.

As used herein, the term "aromatic" includes aryl and heteroaryl groups as described generally below and herein.

The term "aliphatic" or "aliphatic group", as used herein, means an optionally substituted straight-chain or branched $C_{1-12}$ hydrocarbon. For example, suitable aliphatic groups include optionally substituted linear, or branched alkyl, alkenyl, alkynyl groups and hybrids thereof. Unless otherwise specified, in various embodiments, aliphatic groups have 1-12, 1-10, 1-8, 1-6, 1-4, 1-3, or 1-2 carbon atoms.

The term "alkyl", used alone or as part of a larger moiety, refers to an optionally substituted straight or branched chain hydrocarbon group having 1-12, 1-10, 1-8, 1-6, 1-4, 1-3, or 1-2 carbon atoms.

The term "alkenyl", used alone or as part of a larger moiety, refers to an optionally substituted straight or branched chain hydrocarbon group having at least one double bond and having 2-12, 2-10, 2-8, 2-6, 2-4, or 2-3 carbon atoms.

The term "alkynyl", used alone or as part of a larger moiety, refers to an optionally substituted straight or branched chain hydrocarbon group having at least one triple bond and having 2-12, 2-10, 2-8, 2-6, 2-4, or 2-3 carbon atoms.

The terms "cycloaliphatic", "carbocycle", "carbocyclyl", "carbocyclo", or "carbocyclic", used alone or as part of a larger moiety, refer to an optionally substituted saturated or partially unsaturated cyclic aliphatic ring system having from 3 to about 14 ring carbon atoms. In some embodiments, the cycloaliphatic group is an optionally substituted monocyclic hydrocarbon having 3-10, 3-8 or 3-6 ring carbon atoms. Cycloaliphatic groups include, without limitation, optionally substituted cyclopropyl, cyclobutyl, cyclopentyl, cyclopentenyl, cyclohexyl, cyclohexenyl, cycloheptyl, cycloheptenyl, cyclooctyl, cyclooctenyl, or cyclooctadienyl. The terms "cycloaliphatic", "carbocycle", "carbocyclyl", "carbocyclo", or "carbocyclic" also include optionally substituted bridged or fused bicyclic rings having 6-12, 6-10, or 6-8 ring carbon atoms, wherein any individual ring in the bicyclic system has 3-8 ring carbon atoms.

The term "cycloalkyl" refers to an optionally substituted saturated ring system of about 3 to about 10 ring carbon atoms. Exemplary monocyclic cycloalkyl rings include cyclopropyl, cyclobutyl, cyclopentyl, cyclohexyl, and cycloheptyl.

The term "cycloalkenyl" refers to an optionally substituted non-aromatic monocyclic or multicyclic ring system containing at least one carbon-carbon double bond and having about 3 to about 10 carbon atoms. Exemplary monocyclic cycloalkenyl rings include cyclopentenyl, cyclohexenyl, and cycloheptenyl.

The terms "haloaliphatic", "haloalkyl", "haloalkenyl" and "haloalkoxy" refer to an aliphatic, alkyl, alkenyl or alkoxy group, as the case may be, which is substituted with one or more halogen atoms. As used herein, the term "halogen" or "halo" means F, Cl, Br, or I. The term "fluoroaliphatic" refers to a haloaliphatic wherein the halogen is fluoro, including perfluorinated aliphatic groups. Examples of fluoroaliphatic groups include, without limitation, fluoromethyl, difluoromethyl, trifluoromethyl, 2-fluoroethyl, 2,2,2-trifluoroethyl, 1,1,2-trifluoroethyl, 1,2,2-trifluoroethyl, and pentafluoroethyl.

The term "heteroatom" refers to one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR+ (as in N-substituted pyrrolidinyl)).

The terms "aryl" and "ar-", used alone or as part of a larger moiety, e.g., "aralkyl", "aralkoxy", or "aryloxyalkyl", refer to an optionally substituted $C_{6-14}$aromatic hydrocarbon moiety comprising one to three aromatic rings. Preferably, the aryl group is a $C_{6-10}$aryl group. Aryl groups include, without limitation, optionally substituted phenyl, naphthyl, or anthracenyl. The terms "aryl" and "ar-", as used herein, also include groups in which an aryl ring is fused to one or more cycloaliphatic rings to form an optionally substituted cyclic structure such as a tetrahydronaphthyl, indenyl, or indanyl ring. The term "aryl" may be used interchangeably with the terms "aryl group", "aryl ring", and "aromatic ring".

An "aralkyl" or "arylalkyl" group comprises an aryl group covalently attached to an alkyl group, either of which independently is optionally substituted. Preferably, the aralkyl group is $C_{6-10}arylC_{1-6}alkyl$, including, without limitation, benzyl, phenethyl, and naphthylmethyl.

The terms "heteroaryl" and "heteroar-", used alone or as part of a larger moiety, e.g., "heteroaralkyl", or "heteroaralkoxy", refer to groups having 5 to 14 ring atoms, preferably 5, 6, 9, or 10 ring atoms; having 6, 10, or 14π electrons shared in a cyclic array; and having, in addition to carbon atoms, from one to five heteroatoms. In some embodiments, the heteroaryl group has 5-10 ring atoms, having, in addition to carbon atoms, from one to five heteroatoms. A heteroaryl group may be mono-, bi-, tri-, or polycyclic, preferably mono-, bi-, or tricyclic, more preferably mono- or bicyclic. The term "heteroatom" refers to nitrogen, oxygen, or sulfur, and includes any oxidized form of nitrogen or sulfur, and any quaternized form of a basic nitrogen. For example, a nitrogen atom of a heteroaryl may be a basic nitrogen atom and may also be optionally oxidized to the corresponding N-oxide. When a heteroaryl is substituted by a hydroxy group, it also includes its corresponding tautomer. The terms "heteroaryl" and "heteroar-", as used herein, also include groups in which a heteroaromatic ring is fused to one or more aryl, cycloaliphatic, or heterocycloaliphatic rings. Nonlimiting examples of heteroaryl groups include thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, pteridinyl, indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3 (4H)-one. The term "heteroaryl" may be used interchangeably with the terms "heteroaryl ring", "heteroaryl group", or "heteroaromatic", any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle", "heterocyclyl", "heterocyclic radical", and "heterocyclic ring" are used interchangeably and refer to a stable 4-10 membered ring, preferably a 3- to 8-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or NR+ (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothienyl, piperidinyl, decahydroquinolinyl, oxazolidinyl, piperazinyl, dioxanyl, dioxolanyl, diazepinyl, oxazepinyl, thiazepinyl, morpholinyl, and thiomorpholinyl. A heterocyclyl group may be mono-, bi-, tri-, or polycyclic, preferably mono-, bi-, or tricyclic, more preferably mono- or bicyclic. The term "heterocyclylalkyl" refers to an alkyl group substituted by a heterocyclyl, wherein the alkyl and heterocyclyl portions independently are optionally substituted. Additionally, a heterocyclic ring also includes groups in which the heterocyclic ring is fused to one or more aryl rings.

As used herein, the term "partially unsaturated" refers to a ring moiety that includes at least one double or triple bond between ring atoms. The term "partially unsaturated" is intended to encompass rings having multiple sites of unsaturation, but is not intended to include aromatic (e.g., aryl or heteroaryl) moieties, as herein defined.

The term "alkylene" refers to a bivalent alkyl group. An "alkylene chain" is a polymethylene group, i.e., $-(CH_2)_{n'}-$, wherein n' is a positive integer, preferably from 1 to 6, from 1 to 4, from 1 to 3, from 1 to 2, or from 2 to 3. An optionally substituted alkylene chain is a polymethylene group in which one or more methylene hydrogen atoms is optionally replaced with a substituent. Suitable substituents include those described below for a substituted aliphatic group and also include those described in the specification herein. It will be appreciated that two substituents of the alkylene group may be taken together to form a ring system. In certain embodiments, two substituents can be taken together to form a 3-7-membered ring. The substituents can be on the same or different atoms.

An alkylene chain also can be optionally interrupted by a functional group. An alkylene chain is "interrupted" by a functional group when an internal methylene unit is interrupted by the functional group. Examples of suitable "interrupting functional groups" are described in the specification and claims herein.

For purposes of clarity, all bivalent groups described herein, including, e.g., the alkylene chain linkers described above, are intended to be read from left to right, with a corresponding left-to-right reading of the formula or structure in which the variable appears.

An aryl (including aralkyl, aralkoxy, aryloxyalkyl and the like) or heteroaryl (including heteroaralkyl and heteroaralkoxy and the like) group may contain one or more substituents and thus may be "optionally substituted". In addition to the substituents defined above and herein, suitable substituents on the unsaturated carbon atom of an aryl or heteroaryl group also include and are generally selected from -halo, $-NO_2$, $-CN$, $-R^+$, $-C(R^+)=C(R^+)_2$, $-C\equiv C-R^+$, $-OR^+$, $-SR^o$, $-S(O)R^o$, $-SO_2R^o$, $-SO_3R^+$, $-SO_2N(R^+)_2$, $-N(R^+)_2$, $-NR^+C(O)R^+$, $-NR^+C(S)R^+$, $-NR^+C(O)N(R^+)_2$, $-NR^+C(S)N(R^+)_2$, $-N(R^+)C(=NR^+)-N(R^+)_2$, $-N(R^+)C(=NR^+)-R^o$, $-NR^+CO_2R^+$, $-NR^+SO_2R^o$, $-NR^+SO_2N(R^+)_2$, $-O-C(O)R^+$, $-O-CO_2R^+$, $-OC(O)N(R^+)_2$, $-C(O)R^+$, $-C(S)R^o$, $-CO_2R^+$, $-C(O)-C(O)R^+$, $-C(O)N(R^+)_2$, $-C(S)N(R^+)_2$, $-C(O)N(R^+)-OR^+$, $-C(O)N(R^+)C(=NR^+)-N(R^+)_2$, $-N(R^+)C(=NR^+)-N(R^+)-C(O)R^+$, $-C(=NR^+)-N(R^+)_2$, $-C(=NR^+)-OR^+$, $-N(R^+)-N(R^+)_2$, $-C(=NR^+)-N(R^+)-OR^+$, $-C(R^o)=N-OR^+$, $-P(O)(R^+)_2$, $-P(O)(OR^+)_2$, $-O-P(O)-OR^+$, and $-P(O)(NR^+)-N(R^+)_2$, wherein $R^+$, independently, is hydrogen or an optionally substituted aliphatic, aryl, heteroaryl, cycloaliphatic, or heterocyclyl group, or two independent occurrences of $R^+$ are taken together with their intervening atom(s) to form an optionally substituted 5-7-membered aryl, heteroaryl, cycloaliphatic, or heterocyclyl ring. Each $R^o$ is an optionally substituted aliphatic, aryl, heteroaryl, cycloaliphatic, or heterocyclyl group.

An aliphatic or heteroaliphatic group, or a non-aromatic carbycyclic or heterocyclic ring may contain one or more substituents and thus may be "optionally substituted". Unless otherwise defined above and herein, suitable substituents on the saturated carbon of an aliphatic or heteroaliphatic group, or of a non-aromatic carbocyclic or heterocyclic ring are selected from those listed above for the unsaturated carbon of an aryl or heteroaryl group and additionally include the following: =O, =S, =C(R*)$_2$, =N—N(R*)$_2$, =N—OR*, =N—NHC(O)R*, =N—NHCO$_2$R°=N—NHSO$_2$R° or =N—R* where R° is defined above, and each R* is independently selected from hydrogen or an optionally substituted $C_{1-6}$ aliphatic group.

In addition to the substituents defined above and herein, optional substituents on the nitrogen of a non-aromatic heterocyclic ring also include and are generally selected from —R$^+$, —N(R$^+$)$_2$, —C(O)R$^+$, —C(O)OR$^+$, —C(O)C(O)R$^+$, —C(O)CH$_2$C(O)R$^+$, —S(O)$_2$R$^+$, —S(O)$_2$N(R$^+$)$_2$, —C(S)N(R$^+$)$_2$, —C(=NH)—N(R$^+$)$_2$, or —N(R$^+$)S(O)$_2$R$^+$; wherein each R$^+$ is defined above. A ring nitrogen atom of a heteroaryl or non-aromatic heterocyclic ring also may be oxidized to form the corresponding N-hydroxy or N-oxide compound. A nonlimiting example of such a heteroaryl having an oxidized ring nitrogen atom is N-oxidopyridyl.

As detailed above, in some embodiments, two independent occurrences of R$^+$(or any other variable similarly defined in the specification and claims herein), are taken together with their intervening atom(s) to form a monocyclic or bicyclic ring selected from 3-13-membered cycloaliphatic, 3-12-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur.

Exemplary rings that are formed when two independent occurrences of R$^+$(or any other variable similarly defined in the specification and claims herein), are taken together with their intervening atom(s) include, but are not limited to the following: a) two independent occurrences of R$^+$(or any other variable similarly defined in the specification or claims herein) that are bound to the same atom and are taken together with that atom to form a ring, for example, N(R$^+$)$_2$, where both occurrences of R$^+$ are taken together with the nitrogen atom to form a piperidin-1-yl, piperazin-1-yl, or morpholin-4-yl group; and b) two independent occurrences of R$^+$(or any other variable similarly defined in the specification or claims herein) that are bound to different atoms and are taken together with both of those atoms to form a ring, for example where a phenyl group is substituted with two occurrences of

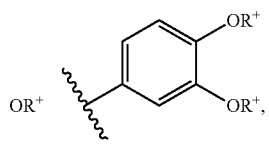

these two occurrences of R$^+$ are taken together with the oxygen atoms to which they are bound to form a fused 6-membered oxygen containing ring:

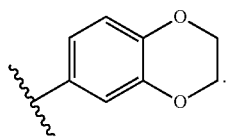 [SMILES: *c1ccc2c(c1)OCCO2]

It will be appreciated that a variety of other rings (e.g., Spiro and bridged rings) can be formed when two independent occurrences of R+ (or any other variable similarly defined in the specification and claims herein) are taken together with their intervening atom(s) and that the examples detailed above are not intended to be limiting.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a 13C- or 14C-enriched carbon are within the scope of this invention. Such compounds are useful, for example, as analytical tools or probes in biological assays.

The terms "stereoisomer", "enantiomer", "diastereomer", "epimer", and "chiral center", are used herein in accordance with the meaning each is given in ordinary usage by those of ordinary skill in the art. Thus, stereoisomers are compounds that have the same atomic connectivity, but differ in the spatial arrangement of the atoms. Enantiomers are stereoisomers that have a mirror image relationship, that is, the stereochemical configuration at all corresponding chiral centers is opposite. Diastereomers are stereoisomers having more than one chiral center, which differ from one another in that the stereochemical configuration of at least one, but not all, of the corresponding chiral centers is opposite. Epimers are diastereomers that differ in stereochemical configuration at only one chiral center.

It is to be understood that, when a disclosed compound has at least one chiral center, the present invention encompasses one enantiomer of the compound, substantially free from the corresponding optical isomer, a racemic mixture of both optical isomers of the compound, and mixtures enriched in one enantiomer relative to its corresponding optical isomer. When a mixture is enriched in one enantiomer relative to its optical isomer, the mixture contains, for example, an enantiomeric excess of at least 50%, 75%, 90%, 95%, 99%, or 99.5%.

The enantiomers of the present invention may be resolved by methods known to those skilled in the art, for example by formation of diastereoisomeric salts which may be separated, for example, by crystallization; formation of diastereoisomeric derivatives or complexes which may be separated, for example, by crystallization, gas-liquid or liquid chromatography; selective reaction of one enantiomer with an enantiomer-specific reagent, for example enzymatic esterification; or gas-liquid or liquid chromatography in a chiral environment, for example on a chiral support for example silica with a bound chiral ligand or in the presence of a chiral solvent. Where the desired enantiomer is converted into another chemical entity by one of the separation procedures described above, a further step is required to liberate the desired enantiomeric form. Alternatively, specific enantiomers may be synthesized by asymmetric synthesis using optically active reagents, substrates, catalysts or solvents, or by converting one enantiomer into the other by asymmetric transformation.

When a disclosed compound has at least two chiral centers, the present invention encompasses a diastereomer substantially free of other diastereomers, an enantiomeric pair of diastereomers substantially free of other stereoisomers, mixtures of diastereomers, mixtures of enantiomeric pairs of diastereomers, mixtures of diastereomers in which one diastereomer is enriched relative to the other diastereomer(s), and mixtures of enantiomeric pairs of diastereomers in which one enantiomeric pair of diastereomers is enriched relative to the other stereoisomers. When a mixture is enriched in one diastereomer or enantiomeric pair of diastereomers pairs relative to the other stereoisomers, the mixture is enriched with the depicted or referenced diastereomer or enantiomeric pair of diastereomers relative to other stereoisomers for the compound, for example, by a molar excess of at least 50%, 75%, 90%, 95%, 99%, or 99.5%.

As used herein, the term "diastereomeric ratio" refers to the ratio between diastereomers which differ in the stereochemical configuration at one chiral center, relative to a second chiral center in the same molecule. By way of example, a chemical structure with two chiral centers provides four possible stereoisomers: R*R, R*S, S*R, and S*S, wherein the asterisk denotes the corresponding chiral center in each stereoisomer. The diastereomeric ratio for such a mixture of stereoisomers is the ratio of one diastereomer and its enantiomer to the other diastereomer and its enantiomer =(R*R+S*S):(R*S+S*R).

One of ordinary skill in the art will recognize that additional stereoisomers are possible when the molecule has more than two chiral centers. For purposes of the present invention, the term "diastereomeric ratio" has identical meaning in reference to compounds with multiple chiral centers as it does in reference to compounds having two chiral centers. Thus, the term "diastereomeric ratio" refers to the ratio of all compounds having R*R or S*S configuration at the specified chiral centers to all compounds having R*S or S*R configuration at the specified chiral centers. For convenience, this ratio is referred to herein as the diastereomeric ratio at the asterisked carbon, relative to the second specified chiral center.

The diastereomeric ratio can be measured by any analytical method suitable for distinguishing between diastereomeric compounds having different relative stereochemical configurations at the specified chiral centers. Such methods include, without limitation, nuclear magnetic resonance (NMR), gas chromatography (GC), and high performance liquid chromatography (HPLC) methods.

The diastereoisomeric pairs may be separated by methods known to those skilled in the art, for example chromatography or crystallization and the individual enantiomers within each pair may be separated as described above. Specific procedures for chromatographically separating diastereomeric pairs of precursors used in the preparation of compounds disclosed herein are provided the examples herein.

3. Description of Exemplary Compounds

In some embodiments, the compounds of the invention are represented by formula (I):

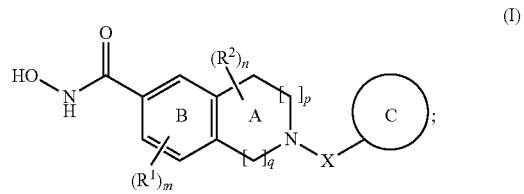

or a pharmaceutically acceptable salt thereof;
wherein:
p is 0-3 and q is 1-4, and the total of p and q is 1-4; provided that p is not 0 when q is 2;
X is —C(O)—, —CH$_2$—, or -L$_1$-R$^3$—V$_1$—;
L$_1$ is a bond or unsubstituted C$_{1-3}$ alkylene chain;
R$^3$ is a 6-membered aromatic ring containing 0-2 nitrogen atoms which is unsubstituted or substituted with 1-2 independent occurrences of R$^4$;
each occurrence of R$^4$ is independently chloro, fluoro, cyano, hydroxy, methoxy, ethoxy, trifluoromethoxy, trifluoromethyl, methyl, or ethyl;
V$_1$ is a bond, —NH—C(O)—, —C(O)—NH—, —NH—S(O)$_2$—, or —NH—C(O)—NH—;
Ring C is a 4-7 membered heterocyclic ring containing one nitrogen atom, wherein the nitrogen atom is not the atom bound to X;
  wherein the nitrogen atom in Ring C is substituted with R$^{9b}$ and Ring C is unsubstituted or substituted by 1-4 occurrences of R$^{5b}$;
ring B is optionally further substituted with m occurrences of R$^1$;
each occurrence of R$^1$ is independently chloro, fluoro, cyano, hydroxy, methoxy, ethoxy, trifluoromethoxy, trifluoromethyl, methyl, or ethyl;
ring A is optionally further substituted with n occurrences of R$^2$;
each occurrence of R$^2$ is independently fluoro, methyl, or trifluoromethyl;
R$^{9b}$ is hydrogen, unsubstituted C(O)—O—C$_{1-6}$ aliphatic, unsubstituted C(O)—C$_{1-6}$ aliphatic, unsubstituted C(O)—C$_{3-10}$ cycloaliphatic, or unsubstituted C$_{1-6}$ aliphatic;
each occurrence of R$^{5b}$ is independently chloro, fluoro, hydroxy, methyl, ethyl, methoxy, ethoxy, trifluoromethyl, trifluoromethoxy, —C(O)NH$_2$, or —CO$_2$H;
m is 0-1; and
n is 0-2.

In some embodiments, the compounds of the invention are represented by formula (I):

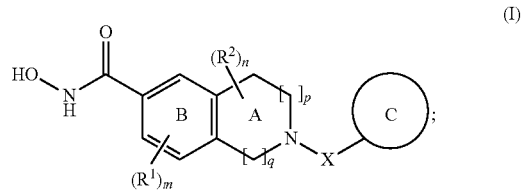

or a pharmaceutically acceptable salt thereof;
wherein:
p is 0-3 and q is 1-4, and the total of p and q is 1-4; provided that p is not 0 when q is 2;
X is —C(O)— or -L$_1$-R$^3$—V$_1$—;
L$_1$ is a bond or unsubstituted C$_{1-3}$ alkylene chain;

R³ is a 6-membered aromatic ring containing 0-2 nitrogen atoms which is unsubstituted or substituted with 1-2 independent occurrences of R⁴;

each occurrence of R⁴ is independently chloro, fluoro, cyano, hydroxy, methoxy, ethoxy, trifluoromethoxy, trifluoromethyl, methyl, or ethyl;

V₁ is a bond, —NH—C(O)—, —C(O)—NH—, —NH—S(O)₂—, or —NH—C(O)—NH—;

Ring C is a 4-7 membered heterocyclic ring containing one nitrogen atom, wherein the nitrogen atom is not the atom bound to X;

wherein the nitrogen atom in Ring C is substituted with $R^{9b}$ and Ring C is unsubstituted or substituted by 1-4 occurrences of $R^{5b}$;

ring B is optionally further substituted with m occurrences of R¹;

each occurrence of R¹ is independently chloro, fluoro, cyano, hydroxy, methoxy, ethoxy, trifluoromethoxy, trifluoromethyl, methyl, or ethyl;

ring A is optionally further substituted with n occurrences of R²;

each occurrence of R² is independently fluoro, methyl, or trifluoromethyl;

$R^{9b}$ is hydrogen, unsubstituted C(O)—O—$C_{1-6}$ aliphatic, unsubstituted C(O)—$C_{1-6}$ aliphatic, unsubstituted C(O)—$C_{3-10}$ cycloaliphatic, or unsubstituted $C_{1-6}$ aliphatic;

each occurrence of $R^{5b}$ is independently chloro, fluoro, hydroxy, methyl, ethyl, methoxy, ethoxy, trifluoromethyl, trifluoromethoxy, —C(O)NH₂, or —CO₂H;

m is 0-1; and n is 0-2.

In some embodiments, the compound of formula (I) is represented by formulas (II-a)-(II-j):

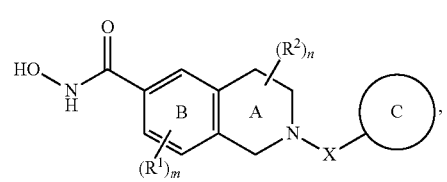
(II-a)

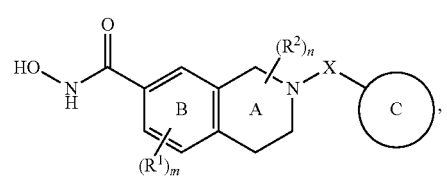
(II-b)

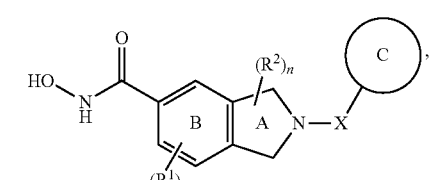
(II-c)

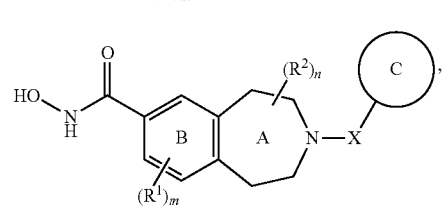
(II-d)

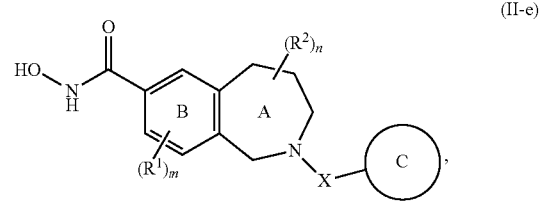
(II-e)

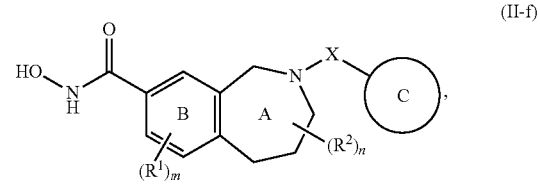
(II-f)

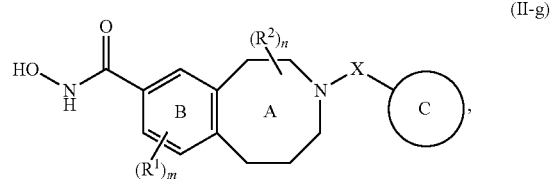
(II-g)

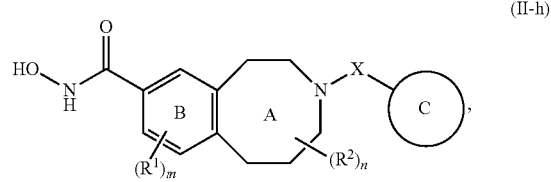
(II-h)

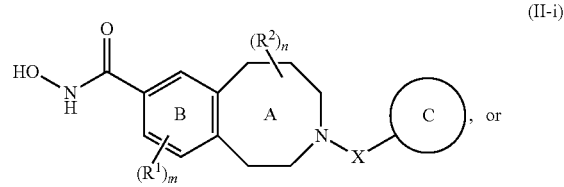
(II-i), or

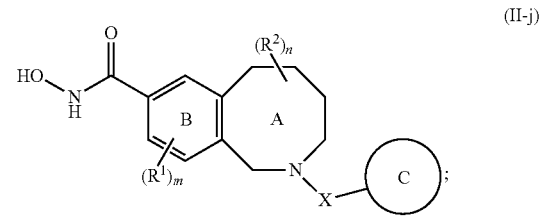
(II-j);

wherein R¹, R², X, m, n, and Ring C have the values described herein. In certain embodiments, the compound of formula (I) is represented by formula (II-a), (II-b), or (II-c) wherein R¹, R², X, m, n, and Ring C have the values described herein. In certain embodiments, the compound of formula (I) is represented by formula (II-a) or (II-c) wherein R¹, R², X, m, n, and Ring C have the values described herein.

In some embodiments, the compound of formula (I) is represented by formulas (III-a)-(III-j):

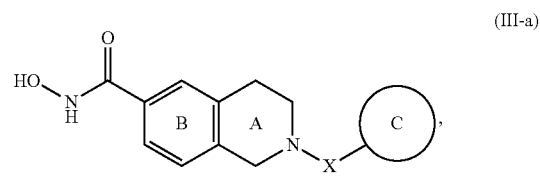
(III-a)

-continued

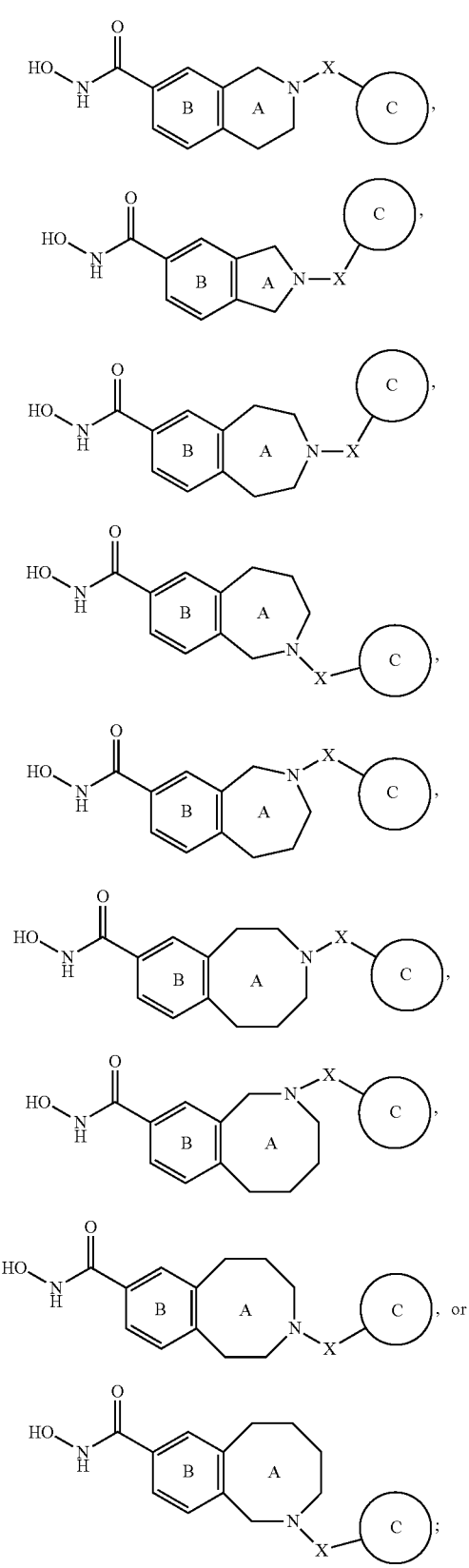

wherein X, and Ring C have the values described herein. In certain embodiments, the compound of formula (I) is represented by formula (III-a), (III-b), or (III-c) wherein X and Ring C have the values described herein. In certain embodiments, the compound of formula (I) is represented by formula (III-a) or (III-c) wherein X and Ring C have the values described herein.

In some embodiments, the compound of formula (I) is represented by formula (IV):

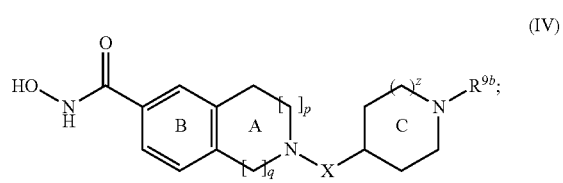

wherein $R^{9b}$, z, X, p, and q have the values described herein, and wherein Ring C can additionally be substituted by one occurrence of $R^{5b}$, wherein $R^{5b}$ has the values described herein.

The values described below for each variable are with respect to any of formulas (I), (II), (III), (IV), (V) or their sub-formulas as described herein.

The variable p is 0-3 and the variable q is 1-4, and the total of p and q is 1-4. In some embodiments, p is 0-3 and q is 1-4, and the total of p and q is 1-4; provided that p is not 0 when q is 2.

In some embodiments, p is 0 and q is 1. In some embodiments, p is 0 and q is 2. In some embodiments, p is 0 and q is 3. In some embodiments, p is 0 and q is 4. In some embodiments, p is 1 and q is 1. In some embodiments, p is 1 and q is 2. In some embodiments, p is 1 and q is 3. In some embodiments, p is 2 and q is 1. In some embodiments, p is 2 and q is 2. In some embodiments, p is 3 and q is 1.

The variable X is —C(O)— or -L$_1$-R$^3$—V$_1$—, wherein L$_1$, R$^3$, and V$_1$ have the values described herein. In some embodiments, X is —C(O)—, —CH$_2$—, or -L$_1$-R$^3$—V$_1$—, wherein L$_1$, R$^3$, and V$_1$ have the values described herein. In some embodiments, X is —C(O)—. In some embodiments, X is —CH$_2$—. In some embodiments, X is -L$_1$-R$^3$—V$_1$—, wherein L$_1$, R$^3$, and V$_1$ have the values described herein. In some embodiments, X is —C(O)—, —CH$_2$—,

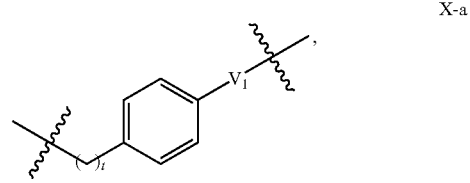

X-a

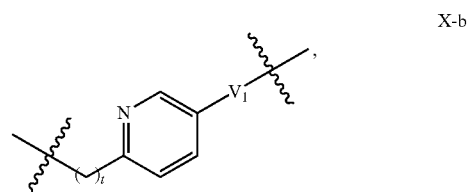

X-b

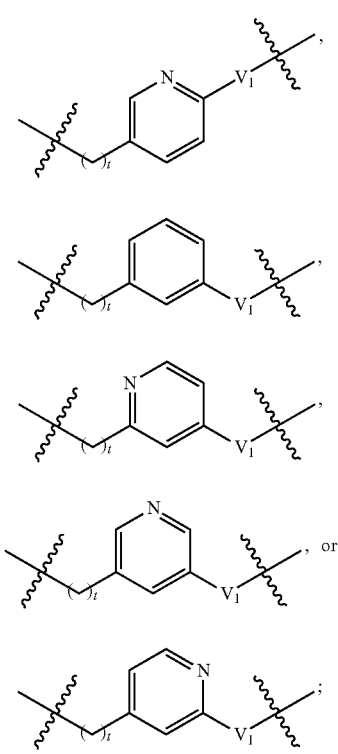
X-c,
X-d,
X-e,
X-f, or
X-g;
wherein $V_1$, Y and t have the values described herein.
In some embodiments, X is -$L_1$-$R^3$—$V_1$—, wherein $L_1$, $R^3$, and $V_1$ have the values described herein. In some embodiments, X is —C(O)—,
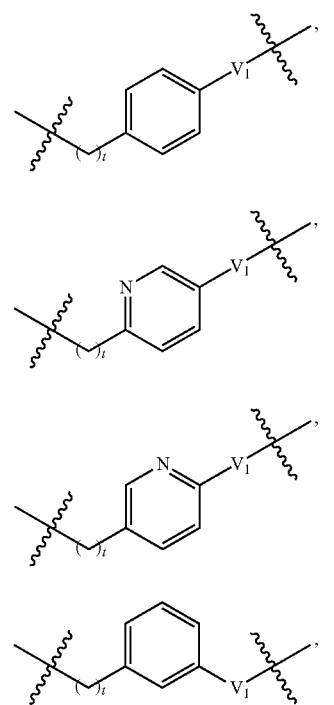
X-a,
X-b,
X-c,
X-d,
X-c,
X-d,
X-e,
X-f, or
X-g;
wherein $V_1$, Y and t have the values described herein.
In certain embodiments, X is —C(O)—, —CH$_2$—,
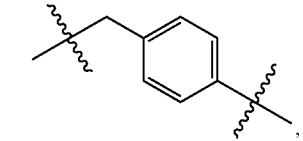
X-i,
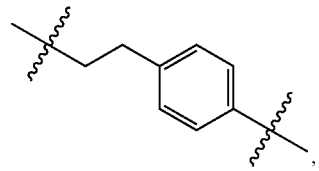
X-ii,
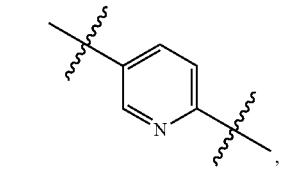
X-iii,
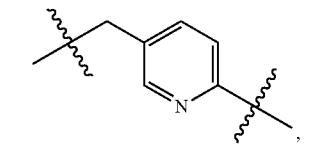
X-iv,
X-v,
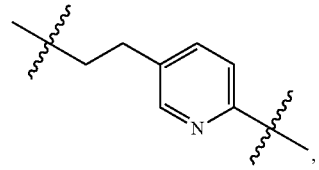
X-vi,

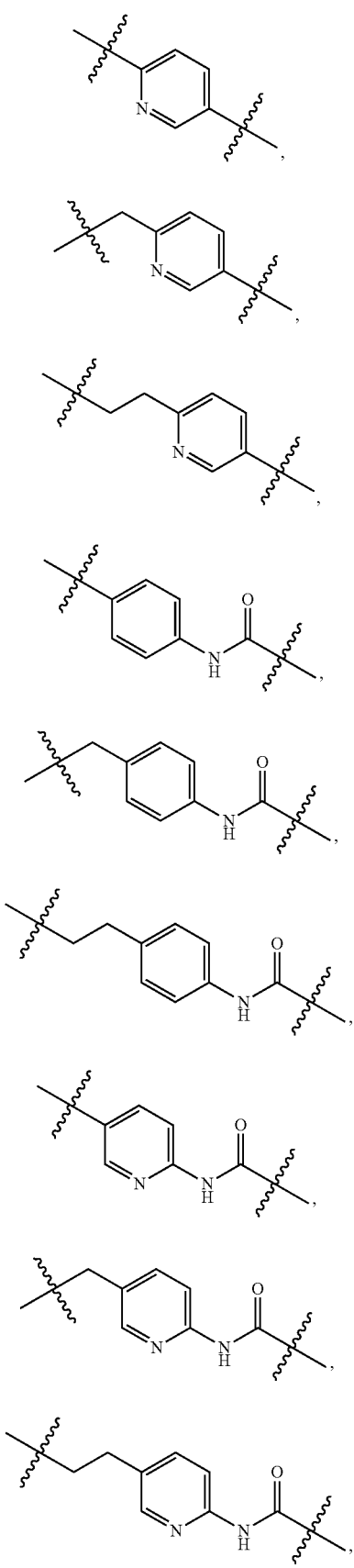
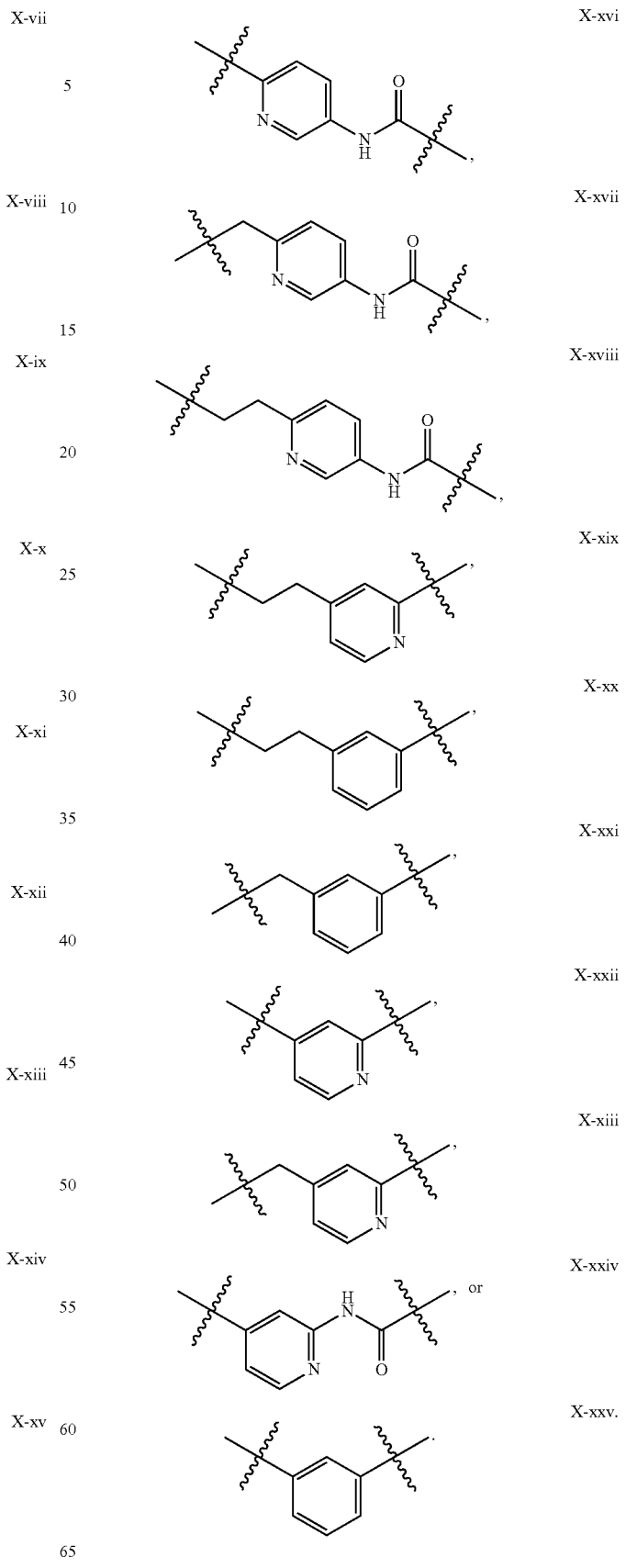
In certain embodiments, X is —C(O)—,

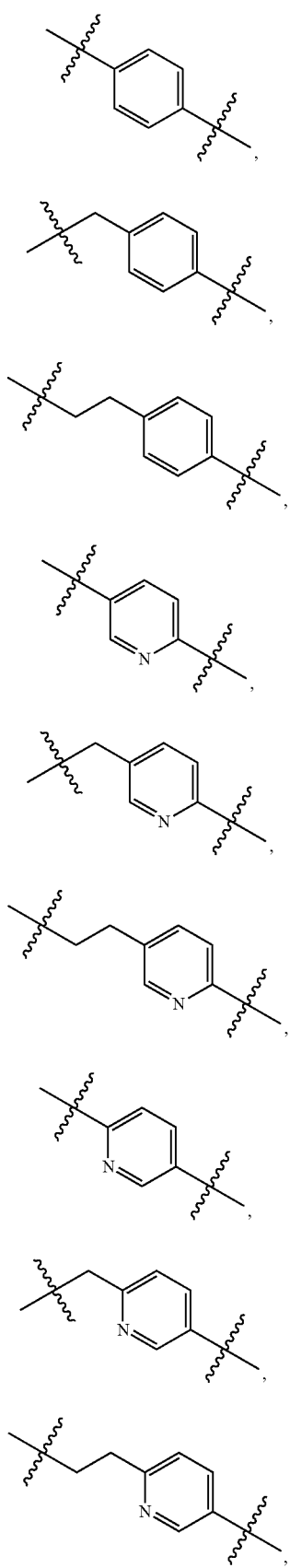
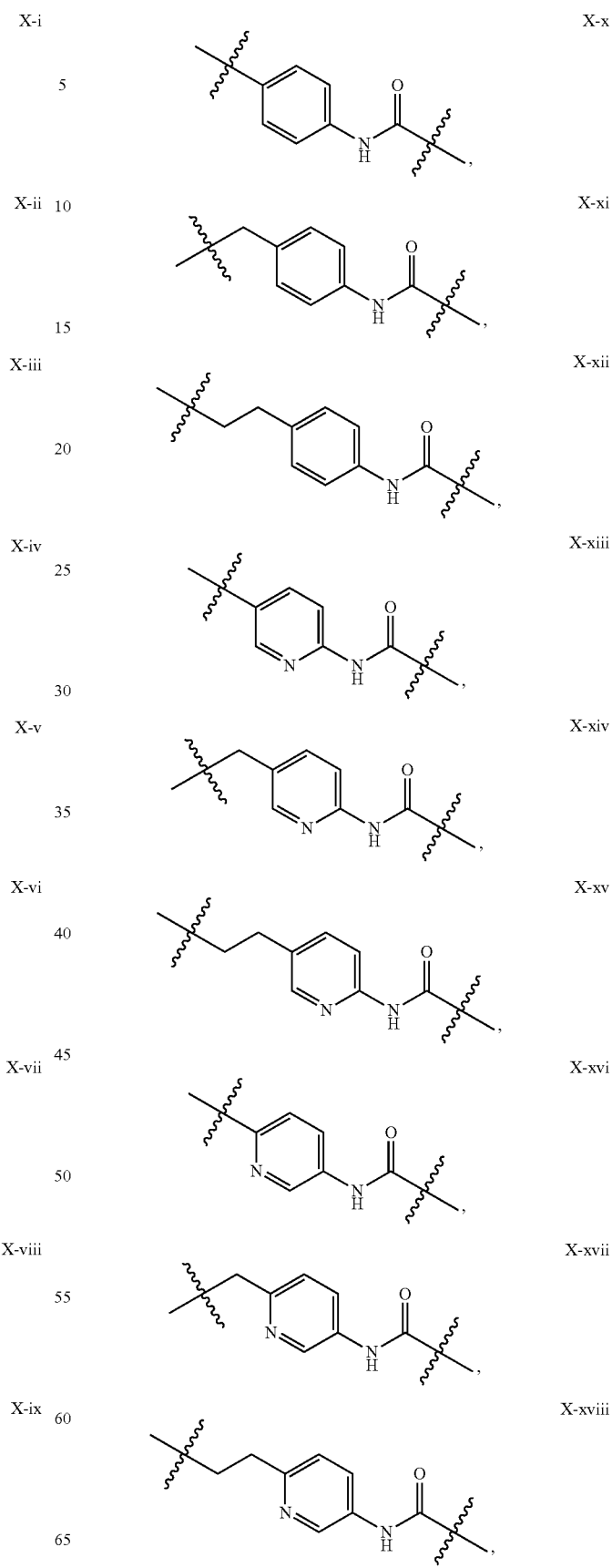

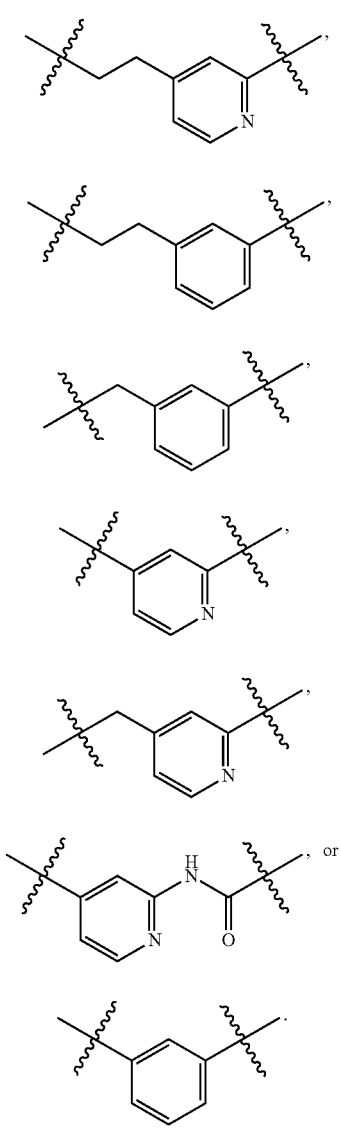

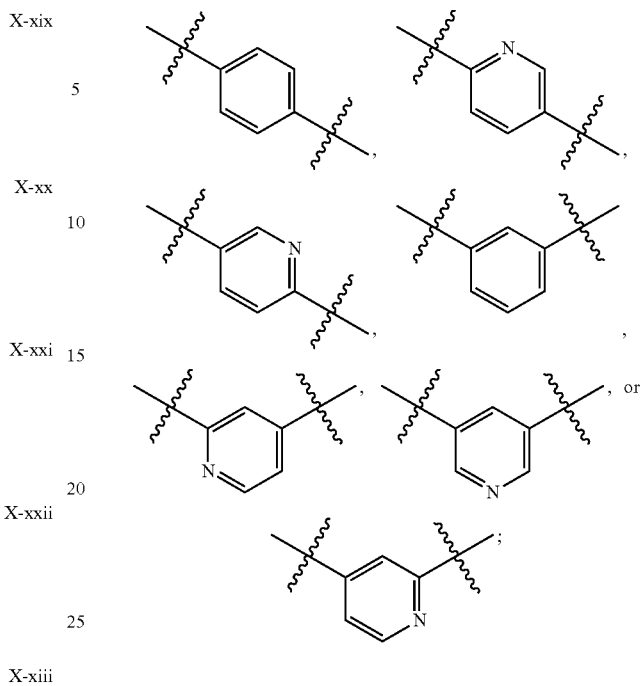

wherein each ring is unsubstituted or substituted with 1-2 independent occurrences of $R^4$.

The variable $R^4$ is chloro, fluoro, cyano, hydroxy, methoxy, ethoxy, trifluoromethoxy, trifluoromethyl, methyl, or ethyl. In some embodiments, $R^4$ is chloro, fluoro, methyl or ethyl.

The variable $V_1$ is a bond, —NH—C(O)—, —C(O)—NH—, —NH—S(O)$_2$—, or —NH—C(O)—NH—. In some embodiments, $V_1$ is a bond or —NH—C(O)—. In certain embodiments, $V_1$ is a bond. In certain embodiments, $V_1$ is —NH—C(O)—.

Ring C is a 4-7 membered heterocyclic ring containing one nitrogen atom, wherein the nitrogen atom is not the atom bound to X, and wherein the nitrogen atom in Ring C is substituted with $R^{9b}$ and Ring C is unsubstituted or substituted by 1-4 occurrences of $R^{5b}$; wherein $R^{9b}$, X, and $R^{5b}$ have the values described herein. In some embodiments, Ring C is a 4-7 membered heterocyclic ring containing one nitrogen atom, wherein the nitrogen atom is not the atom bound to X, and wherein the nitrogen atom in Ring C is substituted with $R^{9b}$ and Ring C is unsubstituted or substituted by 1-2 occurrences of $R^{5b}$; wherein $R^{9b}$, X, and $R^{5b}$ have the values described herein.

In certain embodiments, X is —C(O)—, —CH$_2$—, X-i, X-ii, X-xi, X-xiv, or X-xxiv.

In certain embodiments, X is —C(O)—, —CH$_2$—, X-ii, X-xi, X-xii, X-xxii, X-xxiv, or X-xxv.

In certain embodiments, X is —C(O)—, X-ii, X-xi, X-xii, X-xxii, X-xxiv, or X-xxv.

The variable $L_1$ is a bond or unsubstituted or substituted $C_{1-3}$ alkylene chain. In some embodiments, $L_1$ is a bond, —CH$_2$—, —CH$_2$CH$_2$—, or —CH$_2$CH$_2$CH$_2$—. In certain embodiments, $L_1$ is a bond. In certain embodiments, $L_1$ is —CH$_2$—. In certain embodiments, $L_1$ is —CH$_2$CH$_2$—.

The variable $R^3$ is a 6-membered aromatic ring containing 0-2 nitrogen atoms which is unsubstituted or substituted with 1-2 independent occurrences of $R^4$, wherein $R^4$ has the values described herein. In some embodiments, $R^3$ is phenyl or pyridyl, each of which is unsubstituted or substituted with 1-2 independent occurrences of $R^4$, wherein $R^4$ has the values described herein. In some embodiments, $R^3$ is:

In certain embodiments, Ring C is:

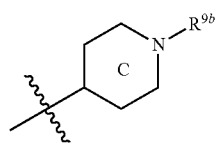

wherein Ring C is unsubstituted or substituted with 1 occurrence of $R^{5b}$, wherein $R^{9b}$ and $R^{5b}$ have the values described herein. In certain embodiments, Ring C is:

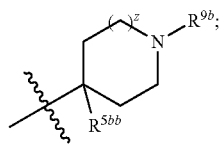

wherein $R^{9b}$, z and $R^{5bb}$ have the values described herein.

Ring B is optionally further substituted with m occurrences of $R^1$, wherein m and $R^1$ have the values described herein.

Each occurrence of the variable $R^1$ is independently chloro, fluoro, cyano, hydroxy, methoxy, ethoxy, trifluoromethoxy, trifluoromethyl, methyl, or ethyl. In some embodiments, each occurrence of the variable $R^1$ is independently chloro, fluoro, methyl, or ethyl.

Ring A is optionally further substituted with n occurrences of $R^2$, wherein n and $R^2$ have the values described herein.

Each occurrence of the variable $R^2$ is independently fluoro, methyl, or trifluoromethyl. In some embodiments, each occurrence of the variable $R^2$ is independently fluoro or methyl.

The variable $R^{9b}$ is hydrogen, unsubstituted C(O)—O—$C_{1-6}$ aliphatic, unsubstituted C(O)—$C_{1-6}$ aliphatic, unsubstituted C(O)—$C_{3-10}$ cycloaliphatic, or unsubstituted $C_{1-6}$ aliphatic. In some embodiments, $R^{9b}$ is unsubstituted $C_{1-6}$ aliphatic. In some embodiments, $R^{9b}$ is hydrogen, methyl, ethyl, isopropyl, or tert-butoxycarbonyl. In some embodiments, $R^{9b}$ is hydrogen, methyl, ethyl, or isopropyl. In some embodiments, $R^{9b}$ is methyl, ethyl, or isopropyl. In certain embodiments, $R^{9b}$ is hydrogen.

Each occurrence of the variable $R^{5b}$ is independently chloro, fluoro, hydroxy, methyl, ethyl, methoxy, ethoxy, trifluoromethyl, trifluoromethoxy, —C(O)NH$_2$, or —CO$_2$H. In some embodiments, each occurrence of the variable $R^{5b}$ is independently chloro, fluoro, methyl, ethyl, trifluoromethyl, —C(O)NH$_2$, or —CO$_2$H. In some embodiments, each occurrence of the variable $R^{5b}$ is independently chloro, fluoro, hydroxy, methyl, or ethyl. In some embodiments, each occurrence of the variable $R^{5b}$ is independently chloro, fluoro, methyl, or ethyl. In certain embodiments, each occurrence of the variable $R^{5b}$ is methyl.

The variable $R^{5bb}$ is hydrogen or methyl. In some embodiments, $R^{5bb}$ is hydrogen. In some embodiments, $R^{5bb}$ is methyl.

The variable m is 0-1. In some embodiments, m is 0. In some embodiments, m is 1.

The variable n is 0-2. In some embodiments, n is 0-1. In some embodiments, n is 0. In some embodiments, n is 1. In some embodiments, n is 2.

The variable t is 0-2. In some embodiments, t is 0-1. In certain embodiments, t is 0. In some embodiments, t is 1. In certain embodiments, t is 2.

The variable z is 0-1. In some embodiments, z is 0. In some embodiments, z is 1.

In certain embodiments, for the compound of formula (I):
p is 0 and q is 1; or p is 1 and q is 1; or p is 0 and q is 2;
m is 0;
n is 0;
Ring C is pyrrolidinyl or piperidinyl;
Ring C is unsubstituted or substituted with one occurrence of $R^{5b}$; and
$R^{5b}$ is methyl.
In embodiments, the compound of formula (I) is represented by formula (IV):

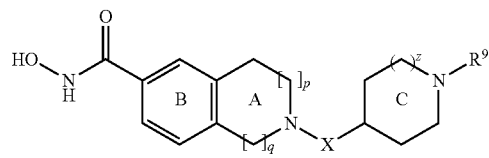

wherein
p is 0 and q is 1; or p is 1 and q is 1; or p is 0 and q is 2;
$R^{9b}$ is hydrogen, methyl, ethyl, isopropyl, or tert-butoxycarbonyl;
X is —C(O)—, —CH$_2$—, X-a, X-b, X-c, X-d, X-e, X-f, or X-g;
Ring C is pyrrolidinyl or piperidinyl;
Ring C is unsubstituted or substituted with one occurrence of $R^{5b}$;
$R^{5b}$ is methyl; and
z has the values described herein.

In certain such embodiments, the compound of formula (I) is represented by formula (IV) wherein p is 0 and q is 1. In certain such embodiments, the compound of formula (I) is represented by formula (IV) wherein p is 0 and q is 1; and X is —C(O)—, —CH$_2$—, X-a, X-c, or X-g. In certain such embodiments, the compound of formula (I) is represented by formula (IV) wherein or p is 1 and q is 1. In certain such embodiments, the compound of formula (I) is represented by formula (IV) wherein or p is 1 and q is 1; and X is —C(O)—, —CH$_2$—, X-a, X-c, or X-g. In certain such embodiments, the compound of formula (I) is represented by formula (IV) wherein p is 0 and q is 2. In certain such embodiments, the compound of formula (I) is represented by formula (IV) wherein p is 0 and q is 2; and X is —C(O)—, —CH$_2$—, X-a, X-c, or X-g.

In certain embodiments, the compound of formula (I) is represented by formula (IV):

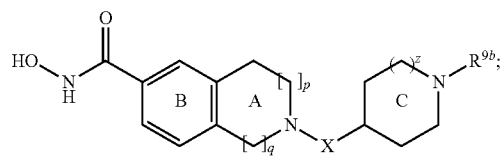

wherein
p is 0 and q is 1; or p is 1 and q is 1; or p is 0 and q is 2;
$R^{9b}$ is hydrogen, methyl, ethyl, isopropyl, or tert-butoxycarbonyl;
X is —C(O)—, —CH$_2$—, X-i, X-ii, X-xi, X-xiv, or X-xxiv;
Ring C is pyrrolidinyl or piperidinyl;
Ring C is unsubstituted or substituted with one occurrence of $R^{5b}$;
$R^{5b}$ is methyl; and
z has the values described herein.

In certain such embodiments, the compound of formula (I) is represented by formula (IV) wherein p is 0 and q is 1. In certain such embodiments, the compound of formula (I) is represented by formula (IV) wherein or p is 1 and q is 1. In certain such embodiments, the compound of formula (I) is represented by formula (IV) wherein p is 0 and q is 2.

In certain embodiments, the compound of formula (I) is represented by:

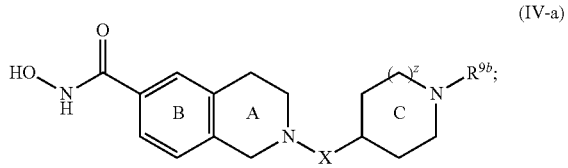

(IV-a)

wherein:

R$^{9b}$ is hydrogen, methyl, ethyl, isopropyl, or tert-butoxycarbonyl;

X is —C(O)—, —CH$_2$—, X-a, X-b, X-c, X-d, X-e, X-f, or X-g;

Ring C is unsubstituted or substituted with one occurrence of R$^{5b}$;

R$^{5b}$ is methyl; and z has the values described herein.

In certain such embodiments, the compound of formula (I) is represented by formula (IV-a) wherein X is —C(O)—, —CH$_2$—, X-a, X-c, or X-g.

In certain embodiments, the compound of formula (I) is represented by:

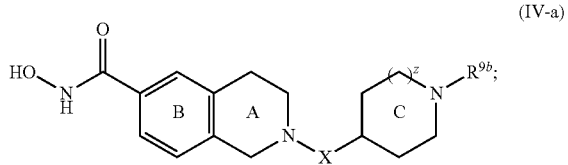

(IV-a)

wherein:

R$^{9b}$ is hydrogen, methyl, ethyl, isopropyl, or tert-butoxycarbonyl;

X is —C(O)—, X-a, X-b, X-c, X-d, X-e, X-f, or X-g;

Ring C is unsubstituted or substituted with one occurrence of R$^{5b}$;

R$^{5b}$ is methyl; and z has the values described herein.

In certain embodiments, the compound of formula (I) is represented by:

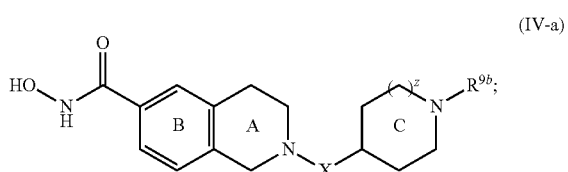

(IV-a)

wherein:

R$^{9b}$ is hydrogen, methyl, ethyl, or isopropyl;

X is —C(O)—, —CH$_2$—, X-a, X-b, X-c, X-d, X-e, X-f, or X-g;

Ring C is unsubstituted or substituted with one occurrence of R$^{5b}$;

R$^{5b}$ is methyl; and z has the values described herein.

In certain embodiments, the compound of formula (I) is represented by:

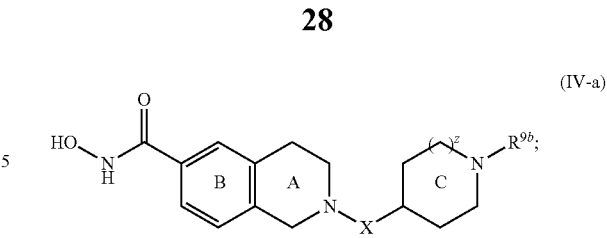

(IV-a)

wherein:

R$^{9b}$ is hydrogen, methyl, ethyl, or isopropyl;

X is —C(O)—, —CH$_2$—, X-a, X-c, or X-g;

Ring C is unsubstituted or substituted with one occurrence of R$^{5b}$;

R$^{5b}$ is methyl; and z has the values described herein.

In certain embodiments, the compound of formula (I) is represented by:

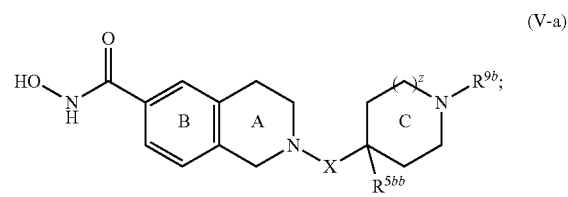

(V-a)

wherein:

R$^{9b}$ is hydrogen, methyl, ethyl, isopropyl, or tert-butoxycarbonyl;

X is —C(O)—, —CH$_2$—, X-ii, X-xi, X-xii, X-xxii, X-xxiv, or X-xxv;

R$^{5bb}$ is hydrogen or methyl; and z has the values described herein.

In certain such embodiments, R$^{5bb}$ is hydrogen and z is 0. In certain such embodiments, R$^{5bb}$ is hydrogen and z is 1. In certain such embodiments, R$^{5bb}$ is methyl and z is 0. In certain such embodiments, R$^{5bb}$ is methyl and z is 1.

In certain embodiments, the compound of formula (I) is represented by:

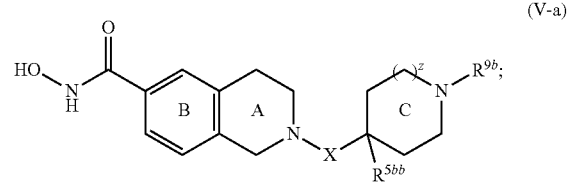

(V-a)

wherein:

R$^{9b}$ is hydrogen, methyl, ethyl, or isopropyl;

X is —C(O)—, —CH$_2$—, X-ii, X-xi, X-xii, X-xxii, X-xxiv, or X-xxv;

R$^{5bb}$ is hydrogen or methyl; and z has the values described herein.

In certain such embodiments, R$^{5bb}$ is hydrogen and z is 0. In certain such embodiments, R$^{5bb}$ is hydrogen and z is 1. In certain such embodiments, R$^{5bb}$ is methyl and z is 0. In certain such embodiments, R$^{5bb}$ is methyl and z is 1.

In certain embodiments, the compound of formula (I) is represented by:

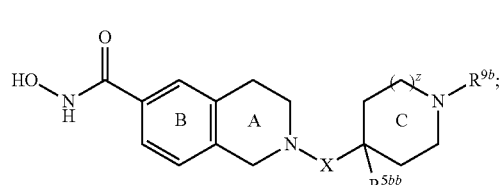

(V-a)

wherein:
R$^{9b}$ is hydrogen, methyl, ethyl, isopropyl, or tert-butoxy-carbonyl;
X is —C(O)—, X-ii, X-xi, X-xii, X-xxii, X-xxiv, or X-xxv;
R$^{5bb}$ is hydrogen or methyl; and
z has the values described herein.

In certain such embodiments, R$^{5bb}$ is hydrogen and z is 0. In certain such embodiments, R$^{5bb}$ is hydrogen and z is 1. In certain such embodiments, R$^{5bb}$ is methyl and z is 0. In certain such embodiments, R$^{5bb}$ is methyl and z is 1.

In certain embodiments, the compound of formula (I) is represented by:

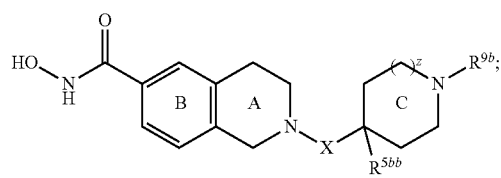

(V-a)

wherein:
R$^{9b}$ is hydrogen, methyl, ethyl, or isopropyl;
X is —C(O)—, X-ii, X-xi, X-xii, X-xxii, X-xxiv, or X-xxv;
R$^{5bb}$ is hydrogen or methyl; and
z has the values described herein.

In certain such embodiments, R$^{5bb}$ is hydrogen and z is 0. In certain such embodiments, R$^{5bb}$ is hydrogen and z is 1. In certain such embodiments, R$^{5bb}$ is methyl and z is 0. In certain such embodiments, R$^{5bb}$ is methyl and z is 1.

In certain embodiments, the compound of formula (I) is represented by:

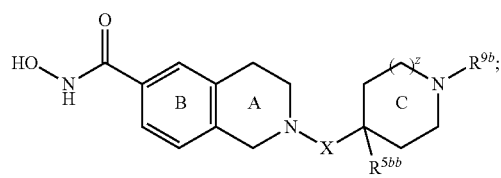

(V-a)

wherein:
R$^{9b}$ is hydrogen, methyl, ethyl, or isopropyl;
X is —C(O)—, —CH$_2$—, X-i, X-ii, X-xi, X-xiv, or X-xxiv;
R$^{5bb}$ is hydrogen or methyl; and
z has the values described herein.

In certain such embodiments, R$^{5bb}$ is hydrogen and z is 0. In certain such embodiments, R$^{5bb}$ is hydrogen and z is 1. In certain such embodiments, R$^{5bb}$ is methyl and z is 0. In certain such embodiments, R$^{5bb}$ is methyl and z is 1.

Representative examples of compounds of formula (I) are shown in Table 1:

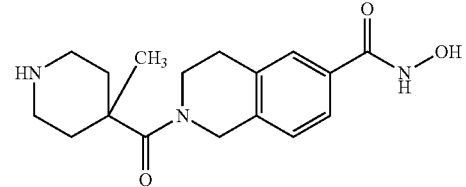

I-1

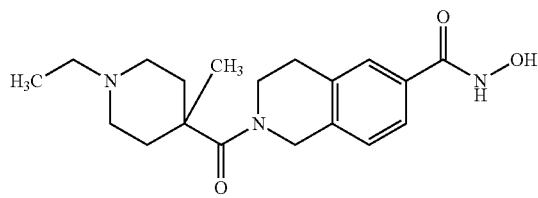

I-2

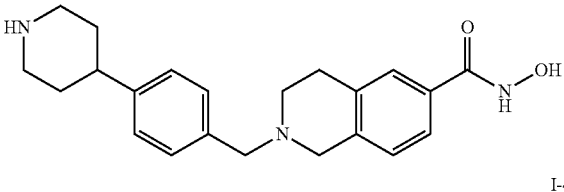

I-3

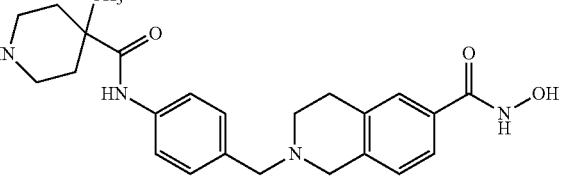

I-4

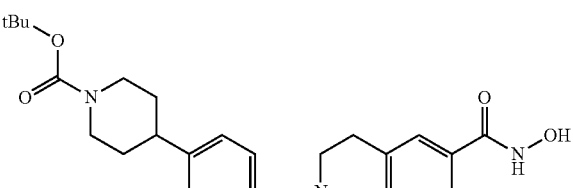

I-5

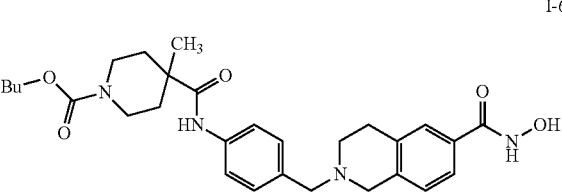

I-6

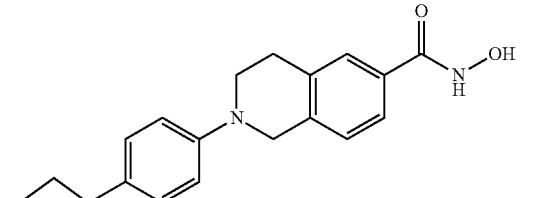

I-7

-continued
I-8
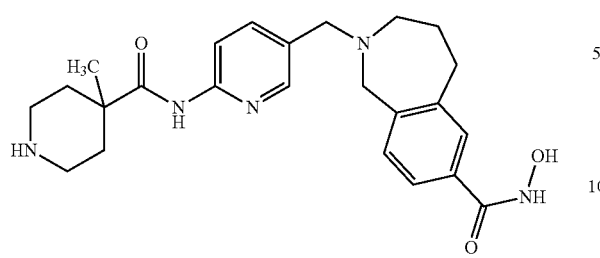
I-9
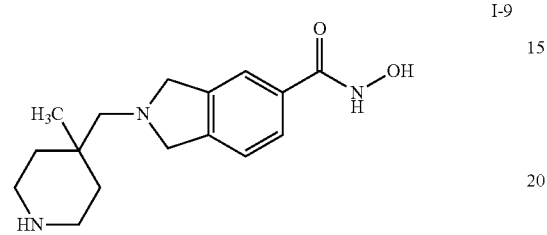
I-10
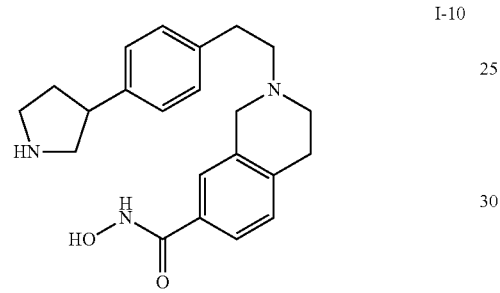
I-11
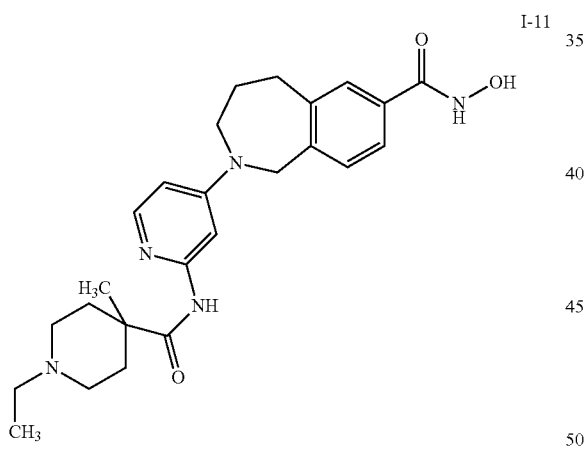
I-12
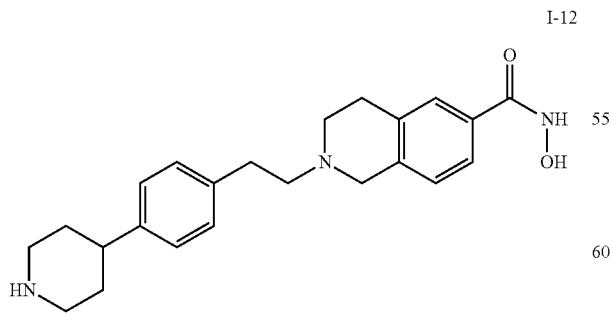
-continued
I-13
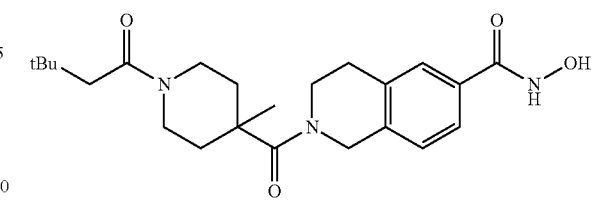
The compounds in Table 1 above may also be identified by the following chemical names:
I-1   N-hydroxy-2-[(4-methylpiperidin-4-yl)carbonyl]-1,2,3,4-tetrahydroisoquinoline-6-carboxamide

| | |
|---|---|
| I-2 | 2-[(1-ethyl-4-methylpiperidin-4-yl)carbonyl]-N-hydroxy-1,2,3,4-tetrahydroisoquinoline-6-carboxamide |
| I-3 | N-hydroxy-2-(4-piperidin-4-ylbenzyl)-1,2,3,4-tetrahydroisoquinoline-6-carboxamide |
| I-4 | N-hydroxy-2-(4-{[(4-methylpiperidin-4-yl)carbonyl]amino}benzyl)-1,2,3,4-tetrahydroisoquinoline-6-carboxamide |
| I-5 | tert-butyl 4-(4-{[6-[(hydroxyamino)carbonyl]-3,4-dihydroisoquinolin-2(1H)-yl]methyl}phenyl)piperidine-1-carboxylate |
| I-6 | tert-butyl 4-{[(4-{[6-[(hydroxyamino)carbonyl]-3,4-dihydroisoquinolin-2(1H)-yl]methyl}phenyl)amino]carbonyl}-4-methylpiperidine-1-carboxylate |
| I-7 | N-hydroxy-2-(4-pyrrolidin-3-ylphenyl)-1,2,3,4-tetrahydroisoquinoline-6-carboxamide |
| I-8 | N-hydroxy-2-[(6-{[(4-methylpiperidin-4-yl)carbonyl]amino}pyridin-3-yl)methyl]-2,3,4,5-tetrahydro-1H-2-benzazepine-7-carboxamide |
| I-9 | N-hydroxy-2-[(4-methylpiperidin-4-yl)methyl]isoindoline-5-carboxamide |
| I-10 | N-hydroxy-2-[2-(4-pyrrolidin-3-ylphenyl)ethyl]-1,2,3,4-tetrahydroisoquinoline-7-carboxamide |
| I-11 | 2-(2-{[(1-ethyl-4-methylpiperidin-4-yl)carbonyl]amino}pyridin-4-yl)-N-hydroxy-2,3,4,5-tetrahydro-1H-2-benzazepine-7-carboxamide |
| I-12 | N-hydroxy-2-[2-(4-piperidin-4-ylphenyl)ethyl]-1,2,3,4-tetrahydroisoquinoline-6-carboxamide |
| I-13 | tert-butyl 4-{[6-[(hydroxyamino)carbonyl]-3,4-dihydroisoquinolin-2(1H)-yl]carbonyl}-4-methylpiperidine-1-carboxylate |

4. General Synthetic Methods and Intermediates

The compounds of the present invention can be prepared by methods known to one of ordinary skill in the art and/or by reference to the schemes shown below and the synthetic examples that follow. Exemplary synthetic routes are set forth in below, and in the Examples. One of ordinary skill in the art will appreciate that transformations shown below can also be carried out on analogous compounds containing one or more substitutents on Rings A and B.

Scheme 1: General route for the synthesis of 2-acyl-N-hydroxy-1,2,3,4-tetrahydroisoquoline-6-carbomide analogs

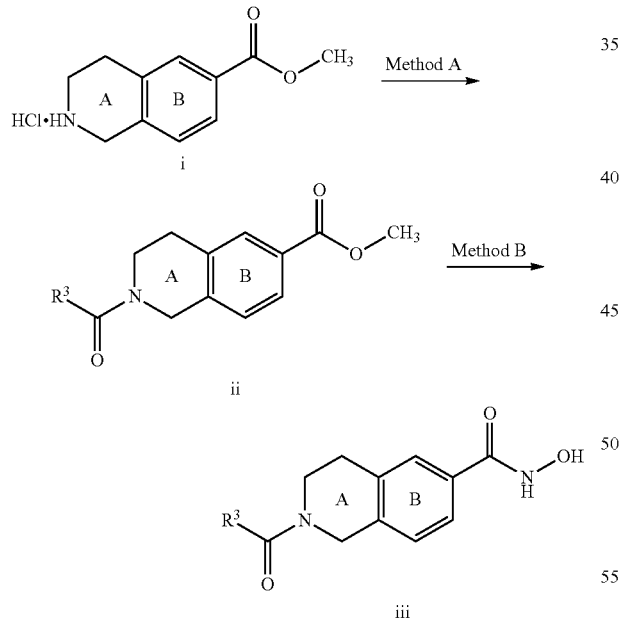

Scheme 1 shows a general route for preparing compounds of formula iii. As shown in scheme 1, methyl 1,2,3,4-tetrahydroisoquinoline-6-carboxylate hydrochloride salt i, is treated with a carboxylic acid, $R^3$—$CO_2H$, using a coupling agent in the presence of a base (Method A). Suitable coupling agents include, but are not limited to, 2-(1H-benzotriazole-1-yl)-1,1,3,3-tetramethyluronium hexafluorophosphate (HBTU), or O-(7-azabenzotriazol-1-yl)-1,1,3,3-tetramethyluronium hexafluorophosphate (HATU). Suitable bases for Method A include, but are not limited to, triethylamine, N,N'-diisoproplyethylamine and N-methylmorpholine. Suitable solvents for Method A include, but are not limited to, dichloromethane (DCM), tetrahydrofuran (THF), N,N'-dimethylformamide (DMF), N-methylpyrrolidone (NMP) or N,N'-dimethylacetamide. Conversion of ii to the corresponding hydroxamate iii is achieved by heating ii in the presence of the potassium salt of hydroxylamine in an appropriate solvent such as methanol (Method B).

Scheme 2: General route for the synthesis of N-hydroxy-2-(2 or 3-substituted-acetyl)-1,2,3,4-tetrahydroisoquinoline-6-carboxamide analogs Scheme 2 shows a general route for preparing compounds of formula vi. Amides of formula iv, where v is 1-2, are prepared by Method A, using either chloroacetic acid or 3-chloroproponic acid, and are then reacted with oxygen ($R^3$—OH) or nitrogen nucleophiles ($R^3$—$NH_2$) in a solvent such as $CH_2Cl_2$ or DMF, in the presence of a base, such as N,N'-diisoproplyethylamine (Method C; see Takikawa et al., Organic Lett. 2007, 9(14):2713-2716; Slee et al., *J. Med. Chem.* 2008, 51(6):1730-1739) to give compounds of formula vi where X is —O— or —NH—. Subsequent conversion of compounds of formula v to the corresponding hydroxamates vi is carried out as described in Scheme 1 using Method B.

Scheme 3: General route for the synthesis of N-hydroxy 2-(substituted sulfonyl)-1,2,3,4-tetrahydroisoquinoline-6-carboxamide analogs

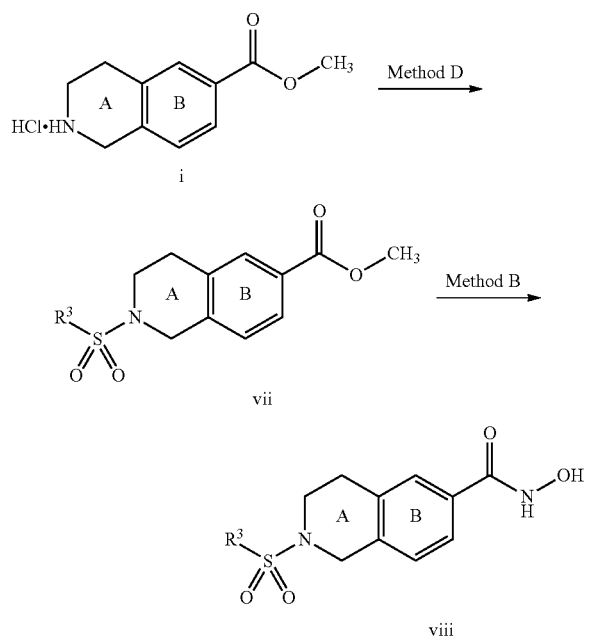

Scheme 3 shows a general route for preparing compounds of formula viii. As shown in Scheme 3, methyl 1,2,3,4-tetrahydroisoquinoline-6-carboxylate hydrochloride salt i is treated with appropriate sulfonyl chloride, $R^3$—$SO_2Cl$, and DMAP in DMF at ambient temperature overnight (Method D). Method D may also be carried out in a solvents such as DCM or N,N'-dimethylacetamide. Subsequent conversion of the resulting compounds of formula vii to the corresponding hydroxamates viii is carried out as described in Scheme 1 using Method B.

Scheme 4: General synthesis of N-hydroxy-2-(substituted-phenylsulfonyl)-1,2,3,4-tetrahydroisoquinoline-6-carboxamide analogs

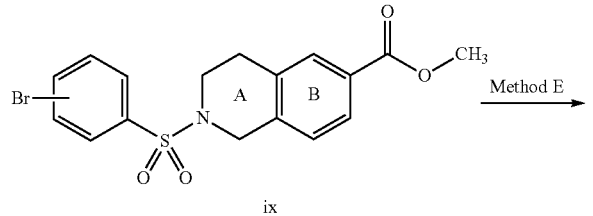

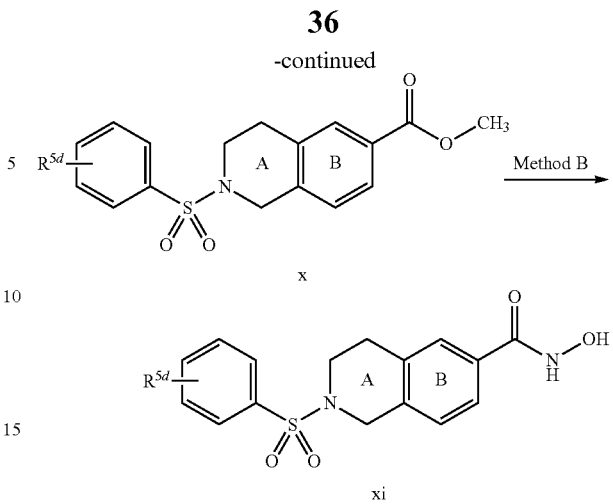

Scheme 4 shows a general route for preparing compounds of formula xi. Sulfonamides of formula ix bearing a pendant aromatic bromide can be prepared as described in Method D, and are then subjected to a Suzuki coupling with a boronic acid, $R^{5d}$—$B(OH)_2$, in the presence of a Pd-catalyst such as $Pd(PPh_3)_4$, and a base such as $Na_2CO_3$ (see Weinstein et al, *Bioorg. Med. Chem. Lett.* 2005 15(5): 1435-1440) to afford sulfonamides of formula x. Subsequent conversion of compounds of formula x to the corresponding hydroxamates of formula xi is carried out as described in Scheme 1 using Method B.

Scheme 5: General route for the synthesis of 2-substituted-N-hydroxy-1,2,3,4-tetrahydroisoquinoline-6-carboxamide analogs

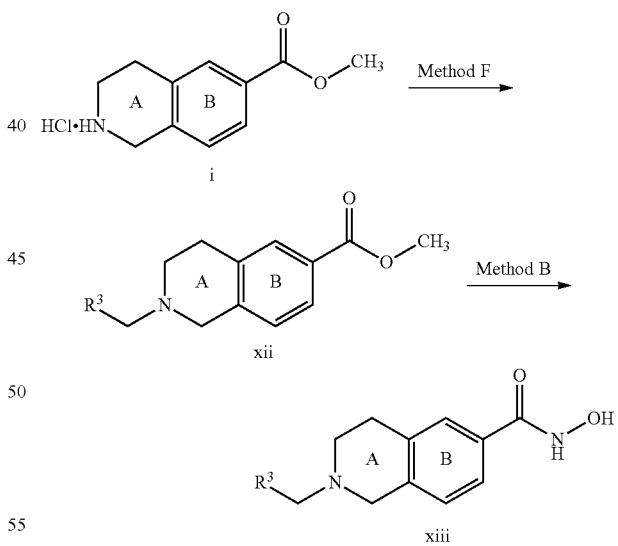

Scheme 5 shows a general route for preparing compounds of formula xiii. As shown in Scheme 5, methyl 1,2,3,4-tetrahydroisoquinoline-6-carboxylate hydrochloride salt i is treated with an appropriate alkyl halide ($R^3$—$CH_2$—Br or $R^3$—$CH_2$—Cl), in the presence of a suitable base such as $Et_3N$ in a solvent such as DMF (Method F) to afford compounds of formula xii. Alternatively, a reductive alkylation with either a ketone or aldehyde employing reducing agents such as sodium triacetoxyborohydride can be used to afford compounds of formula xii (Method L). Subsequent conversion of compounds of formula xii to the corresponding hydroxamate xiii is carried out as described in Scheme 1 (Method B).

Scheme 6: General route for the synthesis of 2-aryl-N-hydroxy-1,2,3,4-tetrahydroisoquinoline-6-carboxamide analogs

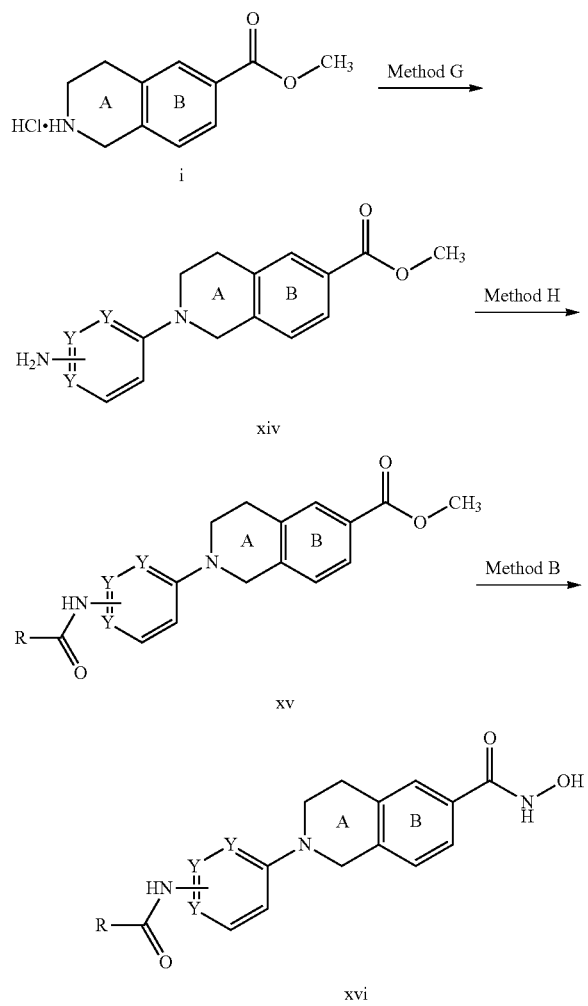

Scheme 6 shows a general route for preparing compounds of formula xvi. As shown in Scheme 6, methyl 1,2,3,4-tetrahydroisoquinoline-6-carboxylate hydrochloride salt i is treated with an appropriate amino substituted aryl or heteroaryl bromide or iodide, in the presence of a suitable base such as K-Ot-Bu and catalyst such as Pd$_2$(dba)$_3$ in a solvent such as toluene (Method G) to afford compounds of formula xiv. The resulting anilines are then acylated in the presence of an acid fluoride or acid chloride in a solvent such as DCM or DMF (Method H) to provide compounds of formula xv. Subsequent conversion of compounds of formula xv to the corresponding hydroxamate xvi is carried out as described in Scheme 1 (Method B).

Scheme 7: Alternative general route for the synthesis of 2-aryl-N-hydroxy-1,2,3,4-tetrahydroisoquinoline-6-carboxamide analogs

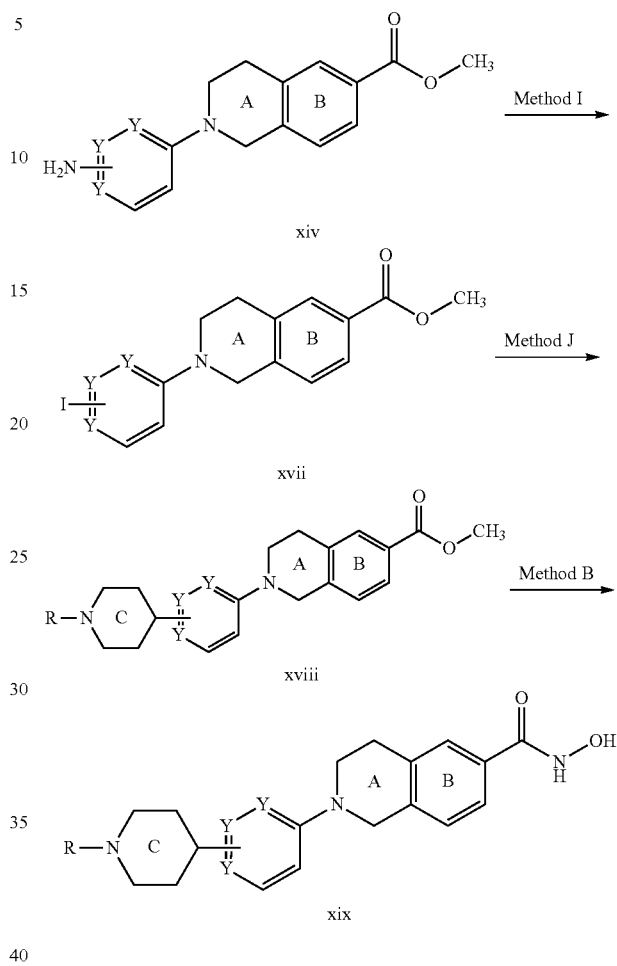

Scheme 7 shows an alternative general route for preparing compounds of formula xix. As shown in Scheme 7, compounds of formula xiv are treated with sodium nitrite in water followed by potassium iodide (Method I) to afford compounds of formula xvi. The resulting iodide is then coupled to a nitrogen containing heterocycle (C) via a 2 step procedure involving a Pd-mediated Heck coupling and reduction (Method J) to provide compounds of formula xviii. Subsequent conversion of compounds of formula xv to the corresponding hydroxamate xix is carried out as described in Scheme 1 (Method B).

5. Uses, Formulation and Administration

As discussed above, the present invention provides compounds and pharmaceutical compositions that are useful as inhibitors of HDAC enzymes, particularly HDAC6, and thus the present compounds are useful for treating proliferative, inflammatory, infectious, neurological or cardiovascular disorders.

The compounds and pharmaceutical compositions of the invention are particularly useful for the treatment of cancer. As used herein, the term "cancer" refers to a cellular disorder characterized by uncontrolled or disregulated cell proliferation, decreased cellular differentiation, inappropriate ability to invade surrounding tissue, and/or ability to establish new growth at ectopic sites. The term "cancer" includes, but is not limited to, solid tumors and bloodborne tumors. The term "cancer" encompasses diseases of skin, tissues, organs, bone, cartilage, blood, and vessels. The term "cancer" further encompasses primary and metastatic cancers.

In some embodiments, therefore, the invention provides the compound of formula (I), or a pharmaceutically acceptable salt thereof, for use in treating cancer. In some embodiments, the invention provides a pharmaceutical composition (as described herein) for the treatment of cancer comprising the compound of formula (I), or a pharmaceutically acceptable salt thereof. In some embodiments, the invention provides the use of the compound of formula (I), or a pharmaceutically acceptable salt thereof, for the preparation of a pharmaceutical composition (as described herein) for the treatment of cancer. In some embodiments, the invention provides the use of an effective amount of the compound of formula (I), or a pharmaceutically acceptable salt thereof, for the treatment of cancer.

Non-limiting examples of solid tumors that can be treated with the disclosed inhibitors include pancreatic cancer; bladder cancer; colorectal cancer; breast cancer, including metastatic breast cancer; prostate cancer, including androgen-dependent and androgen-independent prostate cancer; renal cancer, including, e.g., metastatic renal cell carcinoma; hepatocellular cancer; lung cancer, including, e.g., non-small cell lung cancer (NSCLC), bronchioloalveolar carcinoma (BAC), and adenocarcinoma of the lung; ovarian cancer, including, e.g., progressive epithelial or primary peritoneal cancer; cervical cancer; gastric cancer; esophageal cancer; head and neck cancer, including, e.g., squamous cell carcinoma of the head and neck; melanoma; neuroendocrine cancer, including metastatic neuroendocrine tumors; brain tumors, including, e.g., glioma, anaplastic oligodendroglioma, adult glioblastoma multiforme, and adult anaplastic astrocytoma; bone cancer; and soft tissue sarcoma.

Non-limiting examples of hematologic malignancies that can be treated with the disclosed inhibitors include acute myeloid leukemia (AML); chronic myelogenous leukemia (CML), including accelerated CML and CML blast phase (CML-BP); acute lymphoblastic leukemia (ALL); chronic lymphocytic leukemia (CLL); Hodgkin's disease (HD); non-Hodgkin's lymphoma (NHL), including follicular lymphoma and mantle cell lymphoma; B-cell lymphoma; T-cell lymphoma; multiple myeloma (MM); Waldenstrom's macroglobulinemia; myelodysplastic syndromes (MDS), including refractory anemia (RA), refractory anemia with ringed sideroblasts (RARS), (refractory anemia with excess blasts (RAEB), and RAEB in transformation (RAEB-T); and myeloproliferative syndromes.

In some embodiments, compounds of the invention are suitable for the treatment of breast cancer, lung cancer, ovarian cancer, multiple myeloma, acute myeloid leukemia or acute lymphoblastic leukemia.

In other embodiments, compounds of the invention are suitable for the treatment of inflammatory and cardiovascular disorders including, but not limited to, allergies/anaphylaxis, acute and chronic inflammation, rheumatoid arthritis; autoimmunity disorders, thrombosis, hypertension, cardiac hypertrophy, and heart failure.

Accordingly, in another aspect of the present invention, pharmaceutical compositions are provided, wherein these compositions comprise any of the compounds as described herein, and optionally comprise a pharmaceutically acceptable, carrier, adjuvant or vehicle. In certain embodiments, these compositions optionally further comprise one or more additional therapeutic agents.

It will also be appreciated that certain of the compounds of present invention can exist in free form for treatment, or where appropriate, as a pharmaceutically acceptable derivative thereof. According to the present invention, a pharmaceutically acceptable derivative includes, but is not limited to, pharmaceutically acceptable prodrugs, salts, esters, salts of such esters, or any other adduct or derivative which upon administration to a patient in need is capable of providing, directly or indirectly, a compound as otherwise described herein, or a metabolite or residue thereof.

As used herein, the term "pharmaceutically acceptable salt" refers to those salts which are, within the scope of sound medical judgement, suitable for use in contact with the tissues of humans and lower animals without undue toxicity, irritation, allergic response and the like, and are commensurate with a reasonable benefit/risk ratio. A "pharmaceutically acceptable salt" means any non-toxic salt or salt of an ester of a compound of this invention that, upon administration to a recipient, is capable of providing, either directly or indirectly, a compound of this invention or an inhibitorily active metabolite or residue thereof. As used herein, the term "inhibitorily active metabolite or residue thereof" means that a metabolite or residue thereof is also an inhibitor of HDAC6.

Pharmaceutically acceptable salts are well known in the art. For example, S. M. Berge et al., describe pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}alkyl)_4$ salts. This invention also envisions the quaternization of any basic nitrogen-containing groups of the compounds disclosed herein. Water or oil-soluble or dispersable products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

As described above, the pharmaceutically acceptable compositions of the present invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component (s) of the pharmaceutically acceptable composition, its use is contemplated to be within the scope of this invention. Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

In yet another aspect, a method for treating a proliferative, inflammatory, infectious, neurological or cardiovascular disorder is provided comprising administering an effective amount of a compound, or a pharmaceutical composition to a subject in need thereof. In certain embodiments of the present invention an "effective amount" of the compound or pharmaceutical composition is that amount effective for treating a proliferative, inflammatory, infectious, neurological or cardiovascular disorder, or is that amount effective for treating cancer. In other embodiments, an "effective amount" of a compound is an amount which inhibits binding of HDAC6, and thereby blocks the resulting signaling cascades that lead to the abnormal activity of growth factors, receptor tyrosine kinases, protein serine/threonine kinases, G protein coupled receptors and phospholipid kinases and phosphatases.

The compounds and compositions, according to the method of the present invention, may be administered using any amount and any route of administration effective for treating the disease. The exact amount required will vary from subject to subject, depending on the species, age, and general condition of the subject, the severity of the infection, the particular agent, its mode of administration, and the like. The compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disease being treated and the severity of the disease; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

The pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly (orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient (s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

In some embodiments, a compound of formula (I) or a pharmaceutical composition thereof is administered in conjunction with an anticancer agent. As used herein, the term "anticancer agent" refers to any agent that is administered to a subject with cancer for purposes of treating the cancer. Combination therapy includes administration of the therapeutic agents concurrently or sequentially. Alternatively, the therapeutic agents can be combined into one composition which is administered to the patient.

Non-limiting examples of DNA damaging chemotherapeutic agents include topoisomerase I inhibitors (e.g., irinotecan, topotecan, camptothecin and analogs or metabolites thereof, and doxorubicin); topoisomerase II inhibitors (e.g., etoposide, teniposide, and daunorubicin); alkylating agents (e.g., melphalan, chlorambucil, busulfan, thiotepa, ifosfamide, carmustine, lomustine, semustine, streptozocin, decarbazine, methotrexate, mitomycin C, and cyclophosphamide); DNA intercalators (e.g., cisplatin, oxaliplatin, and carboplatin); DNA intercalators and free radical generators such as bleomycin; and nucleoside mimetics (e.g., 5-fluorouracil, capecitibine, gemcitabine, fludarabine, cytarabine, mercaptopurine, thioguanine, pentostatin, and hydroxyurea).

Chemotherapeutic agents that disrupt cell replication include: paclitaxel, docetaxel, and related analogs; vincristine, vinblastin, and related analogs; thalidomide, lenalidomide, and related analogs (e.g., CC-5013 and CC-4047); protein tyrosine kinase inhibitors (e.g., imatinib mesylate and gefitinib); proteasome inhibitors (e.g., bortezomib); NF-κB inhibitors, including inhibitors of IκB kinase; antibodies which bind to proteins overexpressed in cancers and thereby downregulate cell replication (e.g., trastuzumab, rituximab, cetuximab, and bevacizumab); and other inhibitors of proteins or enzymes known to be upregulated, over-expressed or activated in cancers, the inhibition of which down-regulates cell replication. In certain embodiments, a compound of the invention is administered in conjunction with a proteasome inhibitor.

Another aspect of the invention relates to inhibiting HDAC6, activity in a biological sample or a patient, which method comprises administering to the patient, or contacting said biological sample with a compound of formula (I), or a composition comprising said compound. The term "biological sample", as used herein, generally includes in vivo, in vitro, and ex vivo materials, and also includes, without limitation, cell cultures or extracts thereof; biopsied material obtained from a mammal or extracts thereof; and blood, saliva, urine, feces, semen, tears, or other body fluids or extracts thereof.

Still another aspect of this invention is to provide a kit comprising separate containers in a single package, wherein the inventive pharmaceutical compounds, compositions and/or salts thereof are used in combination with pharmaceutically acceptable carriers to treat disorders, symptoms and diseases where HDAC6 plays a role.

6. Preparation of Exemplary Compounds

| EXPERIMENTAL PROCEDURES Definitions | |
|---|---|
| ATP | adenosine triphosphate |
| D | day |
| DCE | dichloroethane |
| DCM | dichloromethane |
| DIPEA | diisopropylethyl amine |
| DMAP | 4-dimethylaminopyridine |
| DME | dimethyl ether |
| DMF | N,N-dimethylformamide |
| DMSO | dimethylsulfoxide |
| EDTA | ethylenediaminetetraacetic acid |
| EtOAc | ethyl acetate |
| EtOH | ethanol |
| FA | formic acid |
| FBS | fetal bovine serum |
| h | hours |
| HATU | N,N,N',N'-tetramethyl-o-(7-azabenzotriazole-1-yl)uronium hexafluorophosphate |
| HBTU | 2-(7-aza-1H-benzotriazole-1-yl)-1,1,3,3-tetramethyluronium hexafluorophosphate |
| HEPES | N-(2-hydroxyethyl)piperazine-N'-(2-ethanesulfonic acid) |
| HRMS | high resolution mass spectrum |
| IPA | isopropyl alcohol |
| LC-MS | liquid chromatography mass spectrum |
| m/z | mass to charge |
| MTBE | methyl tert-butyl ether |
| Me | methyl |
| MEM | minimum essential media |
| MeOH | methanol |
| min | minutes |
| MS | mass spectrum |
| MWI | microwave irradiation |
| NMM | N-methyl morpholine |
| PBS | phosphate buffered saline |
| rt | room temperature |
| TEA | triethylamine |
| TFA | trifluoroacetic acid |
| TFAA | trifluoroacetic anhydride |
| TFFH | 1,1,3,3-tetramethylfluoroformamidinium hexafluorophosphate |
| THF | tetrahydrofuran |
| TMEDA | N,N,N',N'-tetramethyl-ethane-1,2-diamine |
| Xantphos | 4,5-bis(diphenylphosphino)-9,9-dimethylxanthene |

Analytical Methods

NMR: $^1$H NMR spectra are run on either a 400 MHz Bruker or 300 MHz Bruker unless otherwise stated.

LC-MS: LC-MS spectra are run using an Agilent 1100 LC interfaced to a micromass Waters® Micromass® Zspray™ Mass Detector (ZMD) using the following gradients:

Formic Acid (FA): Acetonitrile containing zero to 100 percent 0.1% formic acid in water.

Ammonium Acetate (AA): Acetonitrile containing zero to 100 percent 10 mM ammonium acetate in water.

HPLC: Preparative HPLC are conducted using 18×150 mm Sunfire C-18 columns eluting with water-MeCN gradients using a Gilson instrument operated by 322 pumps with the UV/visible 155 detector triggered fraction collection set to between 200 nm and 400 nm. Mass gated fraction collection is conducted on an Agilent 1100 LC/MSD instrument.

Example 1 methyl 2-{[1-(tert-butoxycarbonyl)-4-methylpiperidin-4-yl]carbonyl}-1,2,3,4-tetrahydroisoquinoline-6-carboxylate Intermediate 1

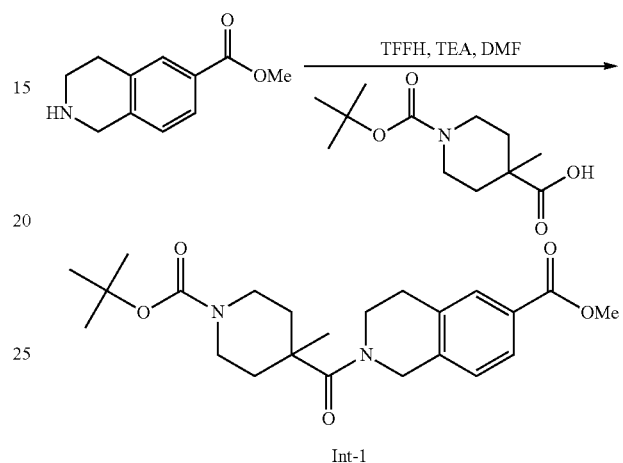

A solution of 1-(tert-butoxycarbonyl)-4-methylpiperidine-4-carboxylic acid (0.830 g, 3.41 mmol) and triethylamine (0.792 mL, 5.68 mmol) in DMF (11.0 mL) was treated with TFFH (1.13 g, 4.26 mmol). The resulting mixture was stirred at rt for 30 min and then methyl 1,2,3,4-tetrahydroisoquinoline-6-carboxylate hydrochloride (0.647 g, 2.84 mmol) and triethylamine (0.792 mL, 5.68 mmol) were added. The reaction mixture was stirred at rt for 2 days and then extracted with EtOAc three times. The combined organic phases were washed with water and brine, dried over Na$_2$SO$_4$, filtered and concentrated. Purification of the resulting residue by column chromatography (SiO$_2$, 0-100% EtOAc in hexane) provided methyl 2-{[1-(tert-butoxycarbonyl)-4-methylpiperidin-4-yl]carbonyl}-1,2,3,4-tetrahydroisoquinoline-6-carboxylate (0.959 g, 82%). LC-MS: (FA) ES+ 439 (M+Na); $^1$H NMR (400 MHz, CDCl$_3$) δ 7.85 (dd, J=10.1, 2.2 Hz, 2H), 7.19 (d, J=8.0 Hz, 1H), 4.79 (s, 2H), 3.95-3.77 (m, 5H), 3.67 (d, J=38.1 Hz, 2H), 3.21 (s, 2H), 2.92 (t, J=5.7 Hz, 2H), 2.24-2.10 (m, 2H), 1.61 (d, J=10.8 Hz, 1H), 1.44 (d, J=5.0 Hz, 10H), 1.33 (d, J=3.6 Hz, 3H).

Example 2 methyl 2-(4-bromobenzyl)-1,2,3,4-tetrahydroisoquinoline-6-carboxylate Intermediate-2

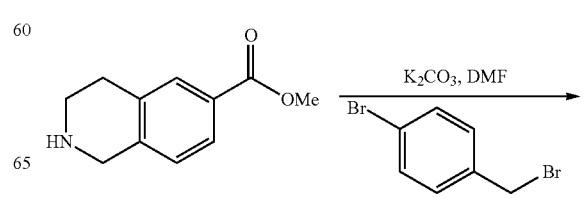

47

-continued

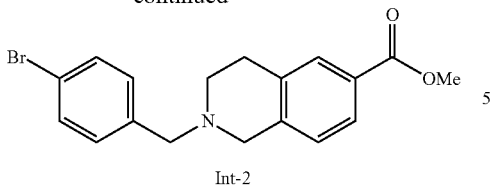
Int-2

To a solution of methyl 1,2,3,4-tetrahydroisoquinoline-6-carboxylate hydrochloride (500.0 mg, 2.00 mmol) in DMF (17.0 mL) was added 4-bromobenzylbromide (604 mg, 2.42 mmol) and $K_2CO_3$ (910 mg, 6.59 mmol). The resulting mixture was stirred overnight at rt. EtOAc and water were added, and the phases were separated. The organic phase was dried over $Na_2SO_4$, filtered and concentrated. The resulting residue was purified by column chromatography ($SiO_2$, 0-40% EtOAc in hexane) to give methyl 2-(4-bromobenzyl)-1,2,3,4-tetrahydroisoquinoline-6-carboxylate (753 mg, 100%). LC-MS: (FA) ES+ 361; $^1$H NMR (300 MHz, $CDCl_3$) δ 7.86-7.70 (m, 2H), 7.46 (dd, J=8.7, 2.1 Hz, 2H), 7.36-7.21 (m, 2H), 7.04 (d, J=8.0 Hz, 1H), 3.89 (d, J=3.8 Hz, 3H), 3.64 (s, 4H), 2.93 (t, J=5.8 Hz, 2H), 2.83-2.64 (m, 2H).

Example 3 methyl 2-{4-[1-(tert-butoxycarbonyl)piperidin-4-yl]benzyl}-1,2,3,4-tetrahydroisoquinoline-6-carboxylate Intermediate-3

48

Step 1: methyl 2-{4-[1-(tert-butoxycarbonyl)-1,2,3,6-tetrahydropyridin-4-yl]benzyl}-1,2,3,4-tetrahydroisoquinoline-6-carboxylate A solution of methyl 2-(4-bromobenzyl)-1,2,3,4-tetrahydroisoquinoline-6-carboxylate (200.0 mg, 0.600 mmol) and tert-butyl 4-(4,4,5,5-tetramethyl-1,3,2-dioxaborolan-2-yl)-3,6-dihydropyridine-1(2H)-carboxylate (188.8 mg, 0.6107 mmol) in DME (5.15 mL) was treated with $Na_2CO_3$ (2.00 M in water, 0.83 mL, 1.66 mmol). The mixture was degassed and $Pd(Ph_3P)_4$ (13 mg, 0.011 mmol) was added. The reaction mixture was heated under argon at 80° C. overnight. The mixture was then cooled to room temperature and diluted with water. The aqueous phase was extracted twice with EtOAc. The combined organic phases were washed with brine, dried over $Na_2SO_4$, filtered and concentrated. The residue was purified by column chromatography ($SiO_2$, 10-50% EtOAc in hexanes) to give methyl 2-{4-[1-(tert-butoxycarbonyl)-1,2,3,6-tetrahydropyridin-4-yl]benzyl}-1,2,3,4-tetrahydroisoquinoline-6-carboxylate (228 mg, 89%). LC-MS: (FA) ES+ 263.

Step 2: methyl 2-{4-[1-(tert-butoxycarbonyl)piperidin-4-yl]benzyl}-1,2,3,4-tetrahydroisoquinoline-6-carboxylate Intermediate-3

A solution of methyl 2-{4-[1-(tert-butoxycarbonyl)-1,2,3,6-tetrahydropyridin-4-yl]benzyl}-1,2,3,4-tetrahydroisoquinoline-6-carboxylate (228 mg, 0.493 mmol) in MeOH (5.0 mL) was degassed thoroughly and palladium on carbon

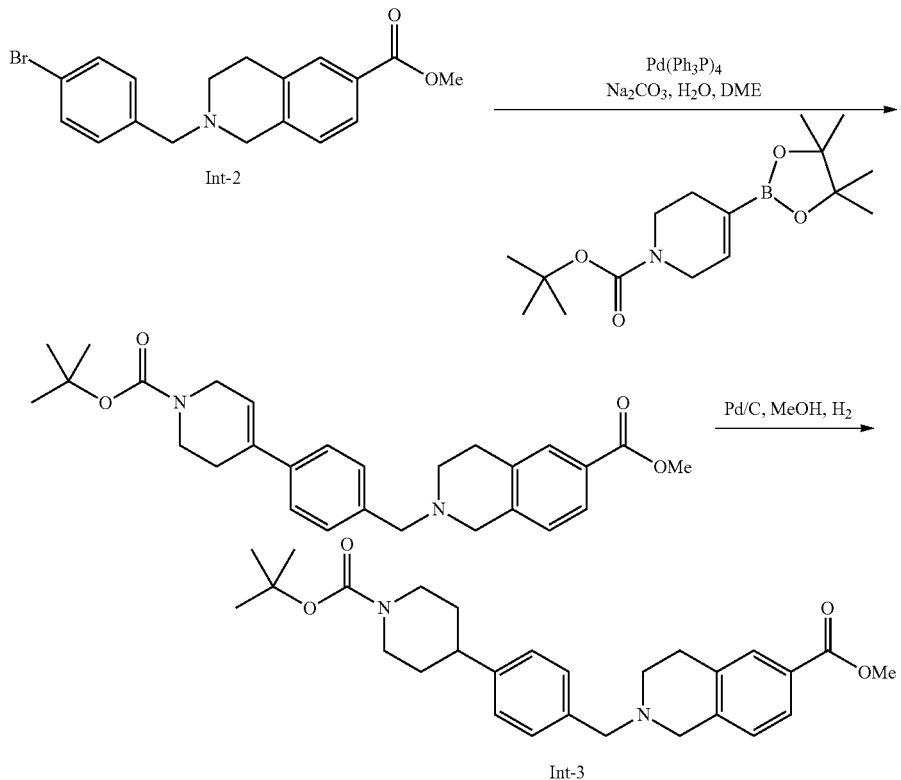

(5% Pd/C, 15.6 mg, 0.0025 mmol) was added. The mixture was stirred at rt under an atmosphere of hydrogen gas for 2 h. The reaction mixture was filtered through a pad of Celite, and the filtrate was concentrated to give methyl 2-{4-[1-(tert-butoxycarbonyl)piperidin-4-yl]benzyl}-1,2,3,4-tetrahydroisoquinoline-6-carboxylate (200 mg, 87%) which was used without purification. LC-MS: (FA) ES+ 465.

Example 4 methyl 2-[4-({[1-(tert-butoxycarbonyl)-4-methylpiperidin-4-yl]carbonyl}amino)benzyl]-1,2,3,4-tetrahydroisoquinoline-6-carboxylate Intermediate-4

(240 mg, 0.670 mmol), Pd$_2$(dba)$_3$ (61 mg, 0.066 mmol), Xantphos (116 mg, 0.200 mmol), and Cs$_2$CO$_3$ (434 mg, 1.33 mmol) in dioxane (10.6 mL) was degassed thoroughly and the reaction vessel was sealed. The mixture was heated at 100° C. overnight and then filtered. The filtrate was concentrated. The resulting residue was purified by column chromatography (SiO$_2$, 0-90% EtOAc in hexane) to give methyl 2-[4-({[1-(tert-butoxycarbonyl)-4-methylpiperidin-4-yl]carbonyl}amino)benzyl]-1,2,3,4-tetrahydroisoquinoline-6-carboxylate (160 mg, 46%). LC-MS: (FA) ES+ 522; $^1$H NMR (400 MHz, CDCl$_3$) δ 7.78 (s, 1H), 7.75 (dd, J=8.0, 1.6 Hz,

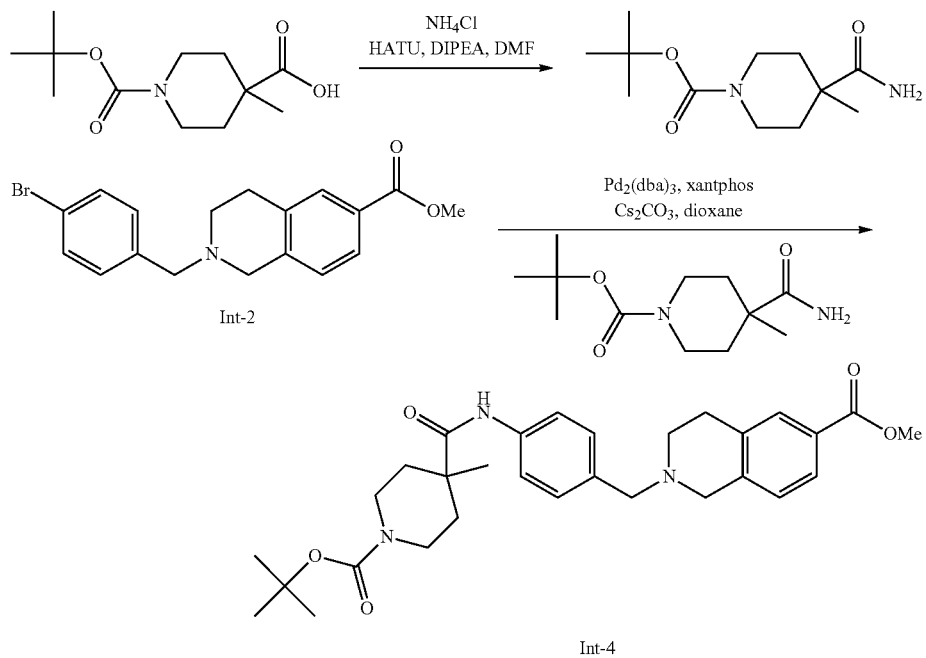

1H), 7.48 (d, J=8.5 Hz, 2H), 7.33 (dd, J=9.3, 7.0 Hz, 3H), 7.01 (t, J=7.3 Hz, 1H), 3.91-3.83 (m, 3H), 3.67 (dd, J=19.7, 4.9 Hz, 5H), 3.40-3.27 (m, 2H), 3.00-2.85 (m, 2H), 2.73 (t, J=5.9 Hz, 2H), 2.13-1.96 (m, 3H), 1.55 (t, J=21.0 Hz, 2H), 1.46 (d, J=5.0 Hz, 9H), 1.31 (d, J=9.9 Hz, 3H).

Step 1: tert-butyl 4-carbamoyl-4-methylpiperidine-1-carboxylate

A solution of 1-(tert-butoxycarbonyl)-4-methylpiperidine-4-carboxylic acid (1.00 g, 4.00 mmol) in DMF (41 mL) and DIPEA (2.9 mL, 17 mmol) was treated with HATU (2.4 g, 6.3 mmol). The solution was stirred for 20 minutes and NH$_4$Cl (0.450 g, 8.40 mmol) was added. The mixture was stirred overnight and then evaporated to dryness. The residue was partitioned between EtOAc (100 mL) and water (150 mL). The phases were separated and the aqueous phase was extracted with EtOAc. The combined organic phases were washed with HCl (1.0 N solution in water), saturated aqueous NaHCO$_3$ solution, water and brine; dried over Na$_2$SO$_4$; filtered and concentrated. The residue was purified by column chromatography (SiO$_2$, 10% MeOH in DCM) to give tert-butyl 4-carbamoyl-4-methylpiperidine-1-carboxylate (781 mg, 78%). LC-MS: (FA) ES+ 265 (M+Na).

Step 2: methyl 2-[4-({[1-(tert-butoxycarbonyl)-4-methylpiperidin-4-yl]carbonyl}amino)benzyl]-1,2,3,4-tetrahydroisoquinoline-6-carboxylate Intermediate-4

A mixture of tert-butyl 4-carbamoyl-4-methylpiperidine-1-carboxylate (178 mg, 0.733 mmol), methyl 2-(4-bromobenzyl)-1,2,3,4-tetrahydroisoquinoline-6-carboxylate Example 5 methyl 2-[(4-methylpiperidin-4-yl)carbonyl]-1,2,3,4-tetrahydroisoquinoline-6-carboxylate.[HCl] Intermediate 5

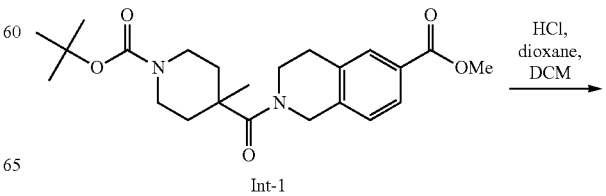

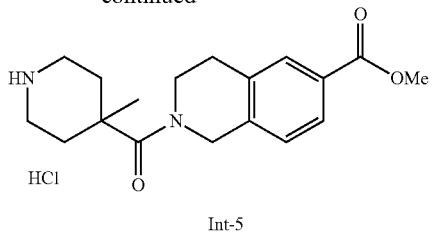

Int-5

A solution of methyl 2-{[1-(tert-butoxycarbonyl)-4-methylpiperidin-4-yl]carbonyl}-1,2,3,4-tetrahydroisoquinoline-6-carboxylate (0.811 g, 1.95 mmol) in DCM (5.0 mL) was treated with a solution of HCl (4.0 M in dioxane, 5.0 mL, 2.0 mmol). The resulting mixture was stirred at rt for 5 h. The mixture was then concentrated to dryness and the residue was twice co-evaporated with toluene. This material, methyl 2-[(4-methylpiperidin-4-yl)carbonyl]-1,2,3,4-tetrahydroisoquinoline-6-carboxylate.[HCl] (0.725 g, ~100%), was suitable for use without further purification. LC-MS: (FA) ES+ 317.

Example 6

The following compounds were prepared in a fashion analogous to that described in Example 5 using the intermediate listed below.

| Starting Carbamate | Product Compound | LC-MS |
|---|---|---|
| I-5 | I-3 | ES+ 366 (AA) |
| I-6 | I-4 | ES+ 423 (FA) |

Example 7 methyl 2-[(1-ethyl-4-methylpiperidin-4-yl)carbonyl]-1,2,3,4-tetrahydroisoquinoline-6-carboxylate Intermediate 6

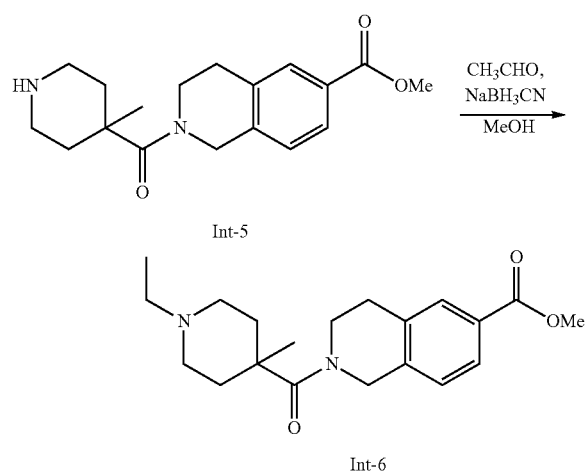

Int-6

A solution of methyl 2-{[1-(tert-butoxycarbonyl)-4-methylpiperidin-4-yl]carbonyl}-1,2,3,4-tetrahydroisoquinoline-6-carboxylate.[HCl] (0.260 g, 0.737 mmol) in MeOH (8.0 mL) was treated with acetaldehyde (0.414 g, 7.37 mmol) and MgSO$_4$ (excess). The reaction mixture was stirred at rt for 1 h, and sodium cyanoborohydride (93 mg, 1.47 mmol) was added in portions. The resulting mixture was stirred for 3 h at rt and then filtered to remove the MgSO$_4$. The filtrate was washed with water and brine, dried over Na$_2$SO$_4$, filtered and concentrated. The resulting residue was purified by column chromatography (SiO$_2$, 0-20% MeOH in DCM) to give methyl 2-[(1-ethyl-4-methylpiperidin-4-yl)carbonyl]-1,2,3,4-tetrahydroisoquinoline-6-carboxylate (55 mg, 22%). LC-MS: (FA) ES+ 345; $^1$H NMR (400 MHz, CDCl$_3$) δ 7.86-7.80 (m, 2H), 7.18 (d, J=7.9 Hz, 1H), 4.78 (s, 2H), 3.89 (s, 3H), 3.88-3.83 (m, 2H), 2.91 (t, J=5.5 Hz, 2H), 2.77-2.67 (m, 2H), 2.42 (q, J=7.2 Hz, 2H), 2.36-2.20 (m, 4H), 1.75-1.65 (m, 2H), 1.30 (s, 3H), 1.09 (t, J=7.2 Hz, 3H).

Example 8 tert-butyl 4-{[6-(hydroxycarbamoyl)-3,4-dihydroisoquinolin-2(1H)-yl]carbonyl}-4-methylpiperidine-1-carboxylate Compound I-13

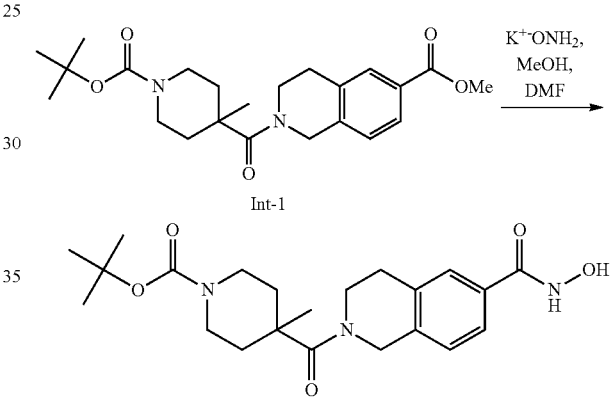

A mixture of hydroxylamine hydrochloride (2.0 g, 29 mmol) in methanol (10 mL) was heated at 90° C. under a dry nitrogen atmosphere until homogeneous. To this heated solution was added a solution of potassium hydroxide (2.85 g, 50.8 mmol) in methanol (6 mL). A precipitate formed on mixing. After heating at 90° C. for 30 minutes, the mixture was cooled to rt and the solids were allowed to settle. The resulting solution was assumed to contain 1.7 M hydroxylamine.potassium salt and was carefully removed by syringe to exclude solids. An aliquot of the above solution (1.95 mL, 3.31 mmol) was added to a solution of methyl 2-{[1-(tert-butoxycarbonyl)-4-methylpiperidin-4-yl]carbonyl}-1,2,3,4-tetrahydroisoquinoline-6-carboxylate (138 mg, 0.331 mmol) in methanol (0.5 mL) and DMF (0.5 mL). After stirring for 3 h at rt, excess reagent was quenched by the addition of acetic acid (0.188 mL, 3.31 mmol). The mixture was concentrated to dryness and the residue was twice co-evaporated with toluene. The crude product was purified by preparative HPLC to afford tert-butyl 4-{[6-(hydroxycarbamoyl)-3,4-dihydroisoquinolin-2(1H)-yl]carbonyl}-4-methylpiperidine-1-carboxylate (103 mg, 74.5%). LC-MS: (FA) ES+ 418; $^1$H NMR (400 MHz, DMSO) δ 11.03 (s, 1H), 9.00 (s, 1H), 7.59-7.52 (m, 2H), 7.28 (d, J=8.0 Hz, 1H), 4.71 (s, 2H), 3.79 (t, J=5.8 Hz, 2H), 3.53-3.44 (m, 2H), 3.15-3.03 (m, 2H), 2.83 (t, J=5.4 Hz, 2H), 2.06-1.96 (m, 2H), 1.47-1.39 (m, 2H), 1.37 (s, 9H), 1.24 (s, 3H).

Example 9

The following compounds were prepared in a fashion analogous to that described in Example 8 using from the appropriate methyl ester intermediate listed below.

| Starting Intermediate | Product Compound | LC-MS |
|---|---|---|
| Int-5 | I-1 | ES+ 318 (FA) |
| Int-6 | I-2 | ES+ 347 (FA) |
| Int-3 | I-5 | ES+ 466 (AA) |
| Int-4 | I-6 | ES+ 523 (FA) |

Example 10

HDAC6 Enzyme Assay

To measure the inhibition of HDAC6 activity, purified human HDAC6 (BPS Bioscience; Cat. No. 5006) is incubated with substrate Ac-Arg-Gly-Lys(Ac)-AMC peptide (Bachem Biosciences; Cat. No. I-1925) for 1 hour at 30° C. in the presence of test compounds or vehicle DMSO control. The reaction is stopped with the HDAC inhibitor trichostatin A (Sigma; Cat. No. T8552) and the amount of Arg-Gly-Lys-AMC generated is quantitated by digestion with trypsin (Sigma; Cat. No. T1426) and subsequent measurement of the amount of AMC released using a fluorescent plate reader (Pherastar; BMG Technologies) set at Ex 340 nm and Em 460 nm. Concentration response curves are generated by calculating the fluorescence increase in test compound-treated samples relative to DMSO-treated controls, and percentage inhibition values at a single concentration or enzyme inhibition ($IC_{50}$) values are determined from those curves. One skilled in the art will appreciate that the values generated either as percentage inhibition at a single concentration or $IC_{50}$ values are subject to experimental variation.

Example 11

Nuclear Extract HDAC Assay

As a screen against Class I HDAC enzymes, HeLa nuclear extract (BIOMOL; Cat. No. KI-140) is incubated with Ac-Arg-Gly-Lys(Ac)-AMC peptide (Bachem Biosciences; Cat. No. I-1925) in the presence of test compounds or vehicle DMSO control. The HeLa nuclear extract is enriched for Class I enzymes HDAC1, -2 and -3. The reaction is stopped with the HDAC inhibitor Trichostatin A (Sigma; Cat. No. T8552) and the amount of Arg-Gly-Lys-AMC generated is quantitated by digestion with trypsin (Sigma; Cat. No. T1426) and subsequent measurement of the amount of AMC released using a fluorescent plate reader (Pherastar; BMG Technologies) set at Ex 340 nm and Em 460 nm. Concentration response curves are generated by calculating the fluorescence increase in test compound-treated samples relative to DMSO-treated controls, and enzyme inhibition ($IC_{50}$) values are determined from those curves.

Example 12

Western Blot and Immunofluorescence Assays

Cellular potency and selectivity of compounds are determined using a published assay (Haggarty et al., *Proc. Natl. Acad. Sci. USA* 2003, 100 (8): 4389-4394) using Hela cells (ATCC cat#CCL-2™) which are maintained in MEM medium (Invitrogen) supplemented with 10% FBS; or multiple myeloma cells RPMI-8226 (ATCC cat#CCL-155™) which are maintained in RPMI 1640 medium (Invitrogen) supplemented with 10% FBS. Briefly, cells are treated with inhibitors for 6 or 24 h and either lysed for Western blotting, or fixed for immunofluorescence analyses. HDAC6 potency is determined by measuring K40 hyperacetylation of alpha-tubulin with an acetylation selective monoclonal antibody (Sigma cat#T7451) in IC50 experiments. Selectivity against Class I HDAC activity is determined similarly using an antibody that recognizes hyperacetylation of histone H4 (Upstate cat#06-866) in the Western blotting assay or nuclear acetylation (Abcam cat#ab21623) in the immunofluorescence assay.

Example 13

In Vivo Tumor Efficacy Model

Female NCr-Nude mice (age 6-8 weeks, Charles River Labs) are aseptically injected into the subcutaneous space in the right dorsal flank with $1.0-5.0 \times 10^6$ cells (SKOV-3, HCT-116, BxPC3) in 100 µL of a 1:1 ratio of serum-free culture media (Sigma Aldrich) and BD Matrigel™ (BD Biosciences) using a 1 mL 26 3/8 gauge needle (Becton Dickinson Ref#309625). Alternatively, some xenograft models require the use of more immunocompromised strains of mice such as CB-17 SCID (Charles River Labs) or NOD-SCID (Jackson Laboratory). Furthermore, some xenograft models require serial passaging of tumor fragments in which small fragments of tumor tissue (approximately 1 mm³) are implanted subcutaneously in the right dorsal flank of anesthetized (3-5% isoflourane/oxygen mixture) NCr-Nude, CB-17 SCID or NOD-SCID mice (age 5-8 weeks, Charles River Labs or Jackson Laboratory) via a 13-ga trocar needle (Popper & Sons 7927). Tumor volume is monitored twice weekly with Vernier calipers. The mean tumor volume is calculated using the formula $V=W^2 \times L/2$. When the mean tumor volume is approximately 200 mm³, the animals are randomized into treatment groups of ten animals each. Drug treatment typically includes the test compound as a single agent, and may include combinations of the test compound and other anti-cancer agents. Dosing and schedules are determined for each experiment based on previous results obtained from pharmacokinetic/pharmacodynamic and maximum tolerated dose studies. The control group will receive vehicle without any drug. Typically, test compound (100-200 µL) is administered via intravenous (27-ga needle), oral (20-ga gavage needle) or subcutaneous (27-ga needle) routes at various doses and schedules. Tumor size and body weight are measured twice a week and the study is terminated when the control tumors reach approximately 2000 mm³, and/or if tumor volume exceeds 10% of the animal body weight or if the body weight loss exceeds 20%.

The differences in tumor growth trends over time between pairs of treatment groups are assessed using linear mixed effects regression models. These models account for the fact that each animal is measured at multiple time points. A separate model is fit for each comparison, and the areas under the curve (AUC) for each treatment group are calculated using the predicted values from the model. The percent decrease in AUC (dAUC) relative to the reference group is then calculated. A statistically significant P value suggests that the trends over time for the two treatment groups are different.

The tumor measurements observed on a date pre-specified by the researcher (typically the last day of treatment) are analyzed to assess tumor growth inhibition. For this analysis, a T/C ratio is calculated for each animal by dividing the tumor measurement for the given animal by the mean tumor measurement across all control animals. The T/C ratios across a treatment group are compared to the T/C ratios of the control group using a two-tailed Welch's t-test. To adjust for multiplicity, a False Discovery Rate (FDR) is calculated for each comparison using the approach described by Benjamini and Hochberg, *J.R. Stat. Soc. B* 1995, 57:289-300.

Example 14

Intrinsic Clearance in Microsomes

The following reagents and stock solutions are required for determination of microsomal clearance.
Reagents:
1. 0.1 M potassium phosphate buffer, pH 7.4:
Stock A (1.0 M): 136.5 g of monobasic potassium phosphate (Sigma #P5379) in 1 L of nanopure water.
Stock B (1.0 M): 174.2 g of dibasic potassium phosphate (Sigma #P8281) in 1 L of nanopure water.
Mix 40.5 mL of stock B+9.5 mL of stock A, adjust pH with monobasic potassium phosphate, qs to 500 mL with nanopure water to give 0.1M potassium phosphate buffer, pH 7.4.
2. Microsomes: (Suggested sources: Xenotech LLC)
All hepatic microsomes contain approximately 20 mg/mL.
3. NADPH: β-nicotinamide adenine dinucleotide phosphate, reduced form (Sigma #N1630)
4. UDPGA: Uridine 5'-Diphosphote Glucuronic Acid, Triamnonium salt (Sigma #U-5625)
5. Alamethicin (Sigma #A-4665-25)
6. $MgCl_2$: Magnesium chloride (Sigma #M8266)
7. DMSO: Dimethyl sulfoxide (Sigma #D4540)
8. 7EC: 7-Ethoxycoumarine (Sigma #E1379), positive control.
9. Carbutamide (Aldrich cat #38157-8), internal standard.
Stock Solutions:
1. 10 mM stock solution of test compound in DMSO
200 μM test solution of test compound: 10 μL of 10 mM test compound stock solution+490 μL of 75% ACN/water
2. 10 mM stock solution of 7-Ethoxycoumarin in DMSO (positive control)
200 μM test solution of 7-Ethoxycoumarine: 10 μL of 10 mM 7EC stock solution+490 μL of 75% ACN/water.
3. 10 mM carbutamide stock (internal standard): Dissolve 2.71 mg of carbutimide in 1 mL DMSO.
1 μM carbutamide solution: 100 μL of 10 mM stock solution in
1 L of acetonitrile, store at 4° C.
4. 3 mM $MgCl_2$ in 0.1 M K-phosphate buffer:
Dissolve 28.5 mg of anhydrous $MgCl_2$ in 100 mL of 0.1 M K-phosphate buffer, pH 7.4.
5. 4× Stock Solution of Cofactors Mixture
16 mM NADPH in 0.1 M K-phosphate buffer, pH 7.4 containing $MgCl_2$
20 mM UDPGA in 0.1 M K-phosphate buffer, pH 7.4 containing $MgCl_2$
Aliquot equal volume of stock solution of NADPH and UDPGA to make the final stock solution of cofactor mixture as follows:
  8 mM NADPH
  10 mM UDPGA
6. Add 1.25 mL of methanol directly to the bottle of alamethicin. Invert 10 times to dissolve the alamethicin. This yields a 20 mg/ml solution of alamethicin.

Procedure: A set volume of microsomal protein and an equal volume of 0.1 M potassium phosphate buffer, pH 7.4 are combined in a vial. Alamethicin is added to achieve a concentration of 50 ug alamethicin per mg of microsomal protein. (i.e. Add 400 ul microsomes to 400 uL of 0.1 M potassium phosphate buffer, pH 7.4 into a vial. Then add 20 ul of the alamethicin stock solution (20 mg/ml).) Invert vial three times and place on ice for 15 minutes. Label 6 "V" bottom 96-well plates (0, 3, 7, 12, 20, and 30 minutes), this corresponds to the six time points in the intrinsic clearance assay. Label an equal number of 2 mL vials (e.g. Polypropylene tubes) as you have test compounds and positive control. In each 2 mL vial place 735 μL of 0.1 M K-phosphate buffer, pH 7.4. Add 375 μL of cofactor solution (NADPH/UDPGA/$MgCl_2$) (stock solution #5) to each 2 mL vial. Add 15 μL of 200 μM test compound or positive control (final concentration in the incubation mixture is 2 μM) to each 2 mL vial. Mix the 2 ml vials with a vortexer and aliquot 75 μL of each vial's content, in duplicate, into 6 labeled 96-well plates. (Plates should be polypropylene or equivalent to minimize binding). Place all plates in a 37° C. incubator for 5 minutes (to warm up to incubation temperature). Also warm the microsomes with alamethicin (from step 3) to 37° C. in a water bath. After the 5 minutes of warming time, add 25 μL of warmed microsomes (from step 10) to each sample well; at this time your incubation begins. (Note: This can best be achieved by using a multipipet or a Multidrop.) Place all plates in the 37° C. incubator for the designated time (0, 3, 7, 12, 20 and 30 minutes). At the end of each incubation time, aliquot 100 μL of 1 μM ice cold carbutamide/ACN solution to each well, this will stop the reaction. (Note: This can be achieved by using a multipipet or a Multidrop.) Once all the incubations have been stopped, place the 96-well plates in a 4° C. refrigerator for 30 minutes. Centrifuge the 96-well plates at 1800×g for 10 minutes. Transfer 100 μL of supernatant into another 96-well plate in descending order of incubation time, 30 minutes to 0 minutes. (Dilution with water may be necessary.) Perform LC/MS/MS analysis.

| Table of Final Concentrations | |
| --- | --- |
| | Final Concentration in Incubation |
| Test compound | 2 μM |
| Positive control | 2 μM |
| S9 | 2.5 mg/mL |
| NADPH | 2 mM |
| UDPGA | 2.5 mM |
| PAPS | 0.10 mM |
| Acetyl CoA | 0.5 mM |
| Alamethicin | 50 ug/ml |
| $MgCl_2$ | 3 mM |
| Buffer | 0.1M |

Calculations:
CL int = (0.693/In Vitro $T_{1/2}$) (Incubation Volume/mg of S9)
(165 mg S9/gram of liver) ($20^a$ gm of liver/kg b · w)
$^a$Scale up factors (gm liver/kg body weight) among different animal species commonly used:
Human          20*
Beagle Dog     25*
Mini Pig       25
Cynomolgus Monkey  30*
Guinea Pig     45
Rat            45*
Mouse          87.5
*Scaling factors were derived from: Lin, J. et. al., *Drug Metab. Dispos.* 1996 (24): 1111-1120.

In certain embodiments, compounds of the invention have the following intrinsic clearances.

| Compound | In Vitro Microsomal Intrinsic Clearance (L/hr/kg) | |
| --- | --- | --- |
| I-1 | Dog CL int | <0.47 |
| | Human CL int | <0.38 |
| | Rat CL int | <0.85 |
| I-2 | Dog CL int | <0.47 |
| | Human CL int | <0.38 |
| | Rat CL int | <0.85 |
| I-13 | Dog CL int | 1.9 |
| | Human CL int | <0.38 |
| | Rat CL int | 2.8 |

As detailed above, compounds of the invention inhibit HDAC6. In certain embodiments, compounds of the invention inhibit HDAC6 with the percent inhibition at 0.37 µM concentration as shown in the table below:

| Compound Number | Percentage Inhibition (%) |
| --- | --- |
| I-13 | 88.76 |
| I-1 | 79.665 |
| I-2 | 78.255 |
| I-3 | 80.66 |
| I-4 | 72.19 |
| I-5 | 46.19 |
| I-6 | 60.96 |

As detailed above, compounds of the invention are selective for HDAC6 over other Class I HDAC enzymes. In some embodiments, the ratio of HDAC IC50 (as obtained in the nuclear extract assay described above) to HDAC6 IC50 is less than 5 (HDAC IC50/HDAC6 IC50). In certain embodiments, the ratio of HDAC IC50 to HDAC6 IC50 is between 5 and 10. In certain embodiments, the ratio of HDAC IC50 to HDAC6 IC50 is between 10 and 100.

While we have described a number of embodiments of this invention, it is apparent that our basic examples may be altered to provide other embodiments, which utilize the compounds and methods of this invention. Therefore, it will be appreciated that the scope of this invention is to be defined by the appended claims rather than by the specific embodiments, which have been represented by way of examples

What is claimed is:

1. A compound of formula (IV):

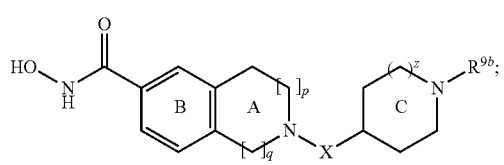

(IV)

wherein:

p is 0-3 and q is 1-4, and the total of p and q is 1-4;

$R^{9b}$ is hydrogen, methyl, ethyl, isopropyl, or tert-butoxycarbonyl;

X is —C(O)—, —CH$_2$—,

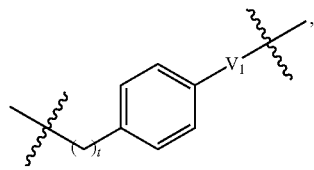

X-a

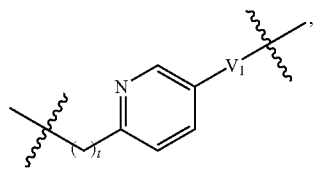

X-b

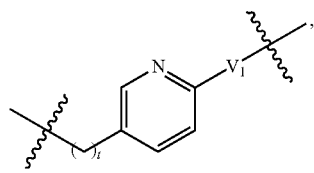

X-c

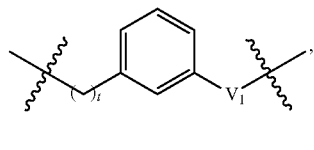

X-d

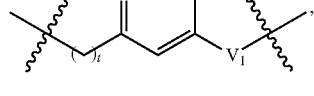

X-e

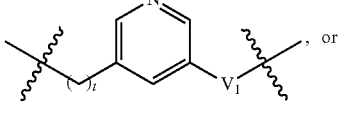

X-f, or

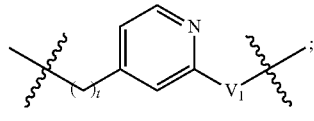

X-g;

$V_1$ is a bond or —NH—C(O)—;

t is 0-2

Ring C is unsubstituted or substituted by 1-4 occurrences of $R^{5b}$;

each occurrence of $R^{5b}$ is independently chloro, fluoro, hydroxy, methyl, ethyl, methoxy, ethoxy, trifluoromethyl, trifluoromethoxy, —C(O)NH$_2$, or —CO$_2$H; and z is 0 or 1.

2. The compound of claim 1, wherein:

p is 0 and q is 1; or p is 1 and q is 1;or p is 0 and q is 2.

3. The compound of claim 1, wherein z is 1;

Ring C is unsubstituted or substituted with one occurrence of $R^{5b}$; and $R^{5b}$ is methyl.

4. The compound of claim 1, represented by formula (V-a):

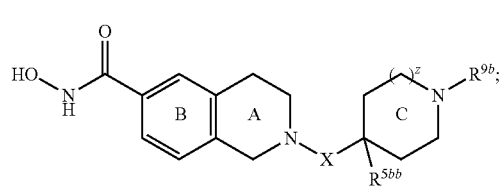
(V-a)

wherein $R^{5bb}$ is hydrogen or methyl.
5. The compound of claim 4, wherein:
$R^{9b}$ is hydrogen, methyl, ethyl, or isopropyl.
6. The compound of claim 4, wherein z is 1.
7. The compound of claim 4, wherein $R^{5bb}$ is methyl.
8. The compound of claim 4, wherein:
X is —C(O)—, —CH$_2$—,

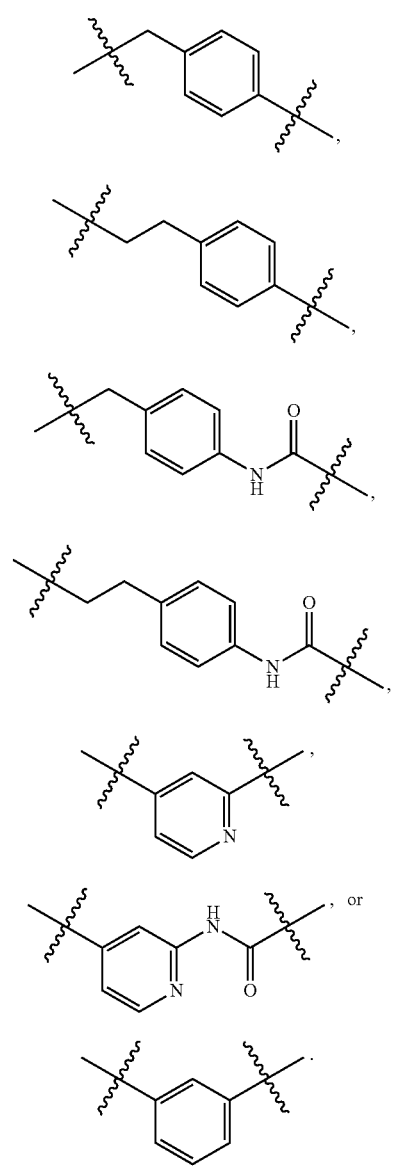

9. The compound of claim 4, wherein:
X is —C(O)—, —CH$_2$—,

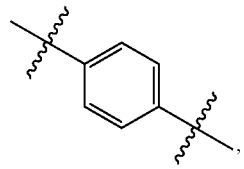
X-i

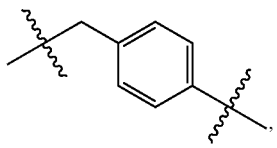
X-ii

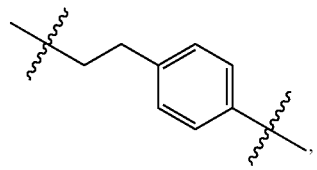
X-iii

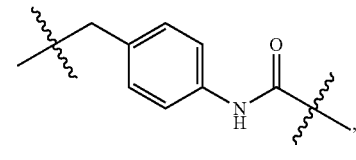
X-xi

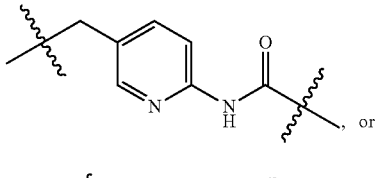
X-xiv

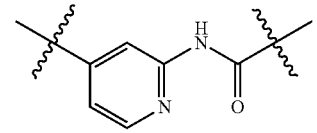
, or

X-xxiv

10. The compound of claim 1, wherein the compound is:
N-hydroxy-2-[(4-methylpiperidin-4-yl)carbonyl]-1,2,3,4-tetrahydroisoquinoline-6-carboxamide,
2-[(1-ethyl-4-methylpiperidin-4-yl)carbonyl]-N-hydroxy-1,2,3,4-tetrahydroisoquinoline-6-carboxamide,
N-hydroxy-2-(4-piperidin-4-ylbenzyl)-1,2,3,4-tetrahydroisoquinoline-6-carboxamide,
N-hydroxy-2-(4-{[(4-methylpiperidin-4-yl)carbonyl]amino}benzyl)-1,2,3,4-tetrahydroisoquinoline-6-carboxamide,
tert-butyl 4-(4-{[6[(hydroxyamino)carbonyl]-3,4-dihydroisoquinolin-2(1H)-yl]methyl}phenyl)piperidine-1-carboxylate,
tert-butyl 4-{[(4-{[6-[(hydroxyamino)carbonyl]-3,4-dihydroisoquinolin-2(1H)-yl]methyl}phenyl)amino]carbonyl}-4-methylpiperidine-1-carboxylate,
N-hydroxy-2-(4-pyrrolidin-3-ylphenyl)-1,2,3,4-tetrahydroisoquinoline-6-carboxamide,
N-hydroxy-2-[(6-{[(4-methylpiperidin-4-yl)carbonyl]amino}pyridin-3-yl)methyl]-2,3,4,5-tetrahydro-1H-2-benzazepine-7-carboxamide,
N-hydroxy-2-[(4-methylpiperidin-4-yl)methyl]isoindoline-5-carboxamide,
N-hydroxy-2-[2-(4-pyrrolidin-3-ylphenyl)ethyl]-1,2,3,4-tetrahydroisoquinoline-7-carboxamide, 2-(2-{[(1-ethyl-4-methylpiperidin-4-yl)carbonyl]amino}pyridin-4-yl)-N-hydroxy-2,3,4,5-tetrahydro-1H-2-benzazepine-7-carboxamide, N-hydroxy-2-[2-(4-piperidin-4-ylphenyl)ethyl]-1,2,3,4-tetrahydroisoquinoline-6-carboxamide, tert-butyl 4-{[6[(hydroxyamino)carbonyl]-3,4-dihydroisoquinolin-2(1H)-yl]carbonyl}-4-methylpiperidine-1-carboxylate, or a pharmaceutically acceptable salt thereof.

11. A pharmaceutical composition comprising a compound of claim 1 and a pharmaceutically acceptable carrier.

* * * * *